(12) United States Patent
Sawa et al.

(10) Patent No.: US 8,515,141 B2
(45) Date of Patent: Aug. 20, 2013

(54) MEDICAL IMAGE PROCESSING APPARATUS AND METHOD FOR DETECTING LOCALLY PROTRUDING LESION

(75) Inventors: Miho Sawa, Hino (JP); Hirokazu Nishimura, Hachioji (JP); Hideki Tanaka, Tama (JP); Ryoko Inoue, Hachioji (JP); Kenji Nakamura, Chiba (JP)

(73) Assignee: Olympus Medical Systems Corp., Tokyo (JP)

( * ) Notice: Subject to any disclaimer, the term of this patent is extended or adjusted under 35 U.S.C. 154(b) by 697 days.

(21) Appl. No.: 12/388,832

(22) Filed: Feb. 19, 2009

(65) Prior Publication Data

US 2009/0220133 A1 Sep. 3, 2009

Related U.S. Application Data

(63) Continuation of application No. PCT/JP2007/061627, filed on Jun. 8, 2007.

(30) Foreign Application Priority Data

Aug. 24, 2006 (JP) ................................. 2006-228192

(51) Int. Cl.
*G06K 9/00* (2006.01)
(52) U.S. Cl.
USPC ............ 382/128; 382/130; 382/131; 382/132
(58) Field of Classification Search
USPC .......................................... 382/128, 130–132
See application file for complete search history.

(56) References Cited

U.S. PATENT DOCUMENTS 6,404,923 B1 * 6/2002 Chaddha ....................... 382/224
7,830,378 B2 * 11/2010 Inoue et al. ................... 345/424
(Continued)

FOREIGN PATENT DOCUMENTS

JP 11-104072 4/1999
JP 2005-192880 7/2005

OTHER PUBLICATIONS

Automated detection of lung nodules in CT scans: Effect of image reconstruction algorithm, Samuel G. Armato, III, Michael B. Altman, and Patrick J. La Rivière, Med. Phys. 30, 461 (2003); (Received Jun. 3, 2002; accepted Dec. 17, 2002; published online Feb. 21, 2003); ISSN: 0094-2405, Published by AAPM.*

(Continued)

*Primary Examiner* — Tony Ko
*Assistant Examiner* — Jori S Reilly-Diakun
(74) *Attorney, Agent, or Firm* — Scully, Scott, Murphy & Presser, P.C.

(57) ABSTRACT

A medical image processing apparatus of the present invention includes: a three-dimensional model estimating section for estimating a three-dimensional model of an object based on a two-dimensional image of an image of the object which is inputted from a medical image pickup apparatus; an image dividing section for dividing the two-dimensional image into a plurality of regions each of which includes at least one or more pixels; a feature value calculation section for calculating a feature value according to a grayscale of each pixel in one region for each of the plurality of regions; and a lesion detection reference setting section for setting lesion detection reference for detecting a locally protruding lesion in the regions of the three-dimensional model which correspond to each of the plurality of regions, based on the feature value according to the grayscale.

18 Claims, 13 Drawing Sheets

(56) References Cited

U.S. PATENT DOCUMENTS

| | | | |
|---|---|---|---|
| 8,165,370 B2* | 4/2012 | Inoue et al. | 382/128 |
| 2005/0111713 A1* | 5/2005 | Jerebko | 382/128 |
| 2007/0019849 A1* | 1/2007 | Kaufman et al. | 382/128 |
| 2007/0165932 A1* | 7/2007 | Nishimura et al. | 382/128 |

OTHER PUBLICATIONS

Segmentation of measured point data using a parametric quadric surface approximation, Yang M.; Lee E., Computer-Aided Design, vol. 31, No. 7, Jun. 1999, pp. 449-457(9).*

* cited by examiner

US 8,515,141 B2

MEDICAL IMAGE PROCESSING APPARATUS AND METHOD FOR DETECTING LOCALLY PROTRUDING LESION

CROSS REFERENCE TO RELATED APPLICATION

This application is a continuation application of PCT/JP2007/061627 filed on Jun. 8, 2007 and claims benefit of Japanese Application No. 2006-228192 filed in Japan on Aug. 24, 2006, the entire contents of which are incorporated herein by this reference.

BACKGROUND OF INVENTION

1. Field of the Invention

The present invention relates to a medical image processing apparatus and a medical image processing method, and more particularly, a medical image processing apparatus and a medical image processing method that achieve the detection of a locally protruding lesion.

2. Description of the Related Art

Conventionally, observations using image pickup equipment such as X-ray diagnostic apparatus, CT, MRI, ultrasound observation apparatus, and endoscope apparatus have been widely made in the medical field. In the image pickup equipment, for example, an endoscope apparatus includes an insertion portion which is insertable into a body cavity, and has operation and configuration such that an image of the inside of a body cavity which is formed by an objective optical system disposed at the distal end portion of the insertion portion is picked up by an image pickup section such as a solid state image pickup device and the image is outputted as an image pickup signal, as the result of which the image of the inside of the body cavity is displayed on a display section such as a monitor based on the image pickup signal. Then, a user observes an organ and the like in the body cavity for example, based on the obtained image of the inside of the body cavity displayed on the display section such as a monitor.

The endoscope apparatus enables a direct pickup of an image of mucous membrane of digestive tract. This allows a user to make a comprehensive observation of the color of mucous membrane, the shape of lesion, the minute structure on the mucous membrane surface, for example. And in recent years, endoscope apparatuses have been proposed in which, based on data of a two-dimensional image corresponding to an picked-up image of the inside of a body cavity, a three-dimensional model of the inside of the body cavity can be estimated.

In addition, in such an endoscope apparatus, the detection of an image that contains a lesion site such as a polyp can be also achieved by using an image processing method described in Japanese Patent Application Laid-Open Publication No. 2005-192880 for example, as an image processing method for detecting a predetermined image which contains a locally protruding lesion.

The image processing method described in Japanese Patent Application Laid-Open Publication No. 2005-192880 extracts the outline of an inputted image and detects a locally protruding lesion in the image based on the outline shape.

SUMMARY OF THE INVENTION

A medical image processing apparatus according to a first aspect of the present invention includes: a three-dimensional model estimating section for estimating a three-dimensional model of an object based on a two-dimensional image of an image of the object which is inputted from a medical image pickup apparatus; an image dividing section for dividing the two-dimensional image into a plurality of regions each of which includes at least one or more pixels; a feature value calculation section for calculating a feature value according to a grayscale of each pixel in one region for each of the plurality of regions; and a lesion detection reference setting section for setting a lesion detection reference for detecting a locally protruding lesion in regions of the three-dimensional model which correspond to each of the plurality of regions, based on the feature value according to the grayscale.

A medical image processing apparatus according to a second aspect of the present invention includes: a three-dimensional model estimating section for estimating a three-dimensional model of an object based on a two-dimensional image of an image of the object which is inputted from a medical image pickup apparatus; an image information extracting section for extracting image information according to a grayscale of each pixel in the two-dimensional image; an image dividing section for dividing the two-dimensional image into a plurality of regions based on the feature value according to the grayscale of each pixel; and a lesion detection reference setting section for setting a lesion detection reference for detecting a locally protruding lesion in regions of the three-dimensional model which correspond to each of the plurality of regions divided by the image dividing section.

A medical image processing apparatus according to a third aspect of the present invention includes: a three-dimensional model estimating section for estimating a three-dimensional model of an object based on a two-dimensional image of an image of the object which is inputted from a medical image pickup apparatus; an image dividing section for dividing the two-dimensional image into a plurality of regions each of which includes at least one or more pixels; an image position detecting section for detecting a positional relationship between the positions of each of the plurality of regions on the two-dimensional image and a predetermined position on the two-dimensional image; and a lesion detection reference setting section for setting a lesion detection reference for detecting a locally protruding lesion in the regions of the three-dimensional model that correspond to each of the plurality of regions, based on the positional relationship detected by the image position detecting section.

A medical image processing method according to a first aspect of the present invention includes: a three-dimensional model estimating step for estimating a three-dimensional model of an object based on a two-dimensional image of an image of the object inputted from a medical image pickup apparatus; an image dividing step for dividing the two-dimensional image into a plurality of regions each of which includes at least one or more pixels; a feature value calculating step for calculating a feature value according to a grayscale of each pixel included in one region for each of the plurality of regions; and a lesion detection reference setting step for setting a lesion detection reference for detecting a locally protruding lesion in the regions of the three-dimensional model that correspond to each of the plurality of regions, based on the feature value according to the grayscale.

A medical image processing method according to a second aspect of the present invention includes: a three-dimensional model estimating step for estimating a three-dimensional model of an object based on a two-dimensional image of an image of the object inputted from a medical image pickup apparatus; an image information extracting step for extracting image information according to the grayscale of each pixel included in the two-dimensional image; an image dividing step for dividing the two-dimensional image into a plurality of regions based on feature value according to the grayscale of each pixel; and a lesion detection reference setting step for setting a lesion detection reference for detecting a locally protruding lesion in the regions of the three-dimensional model that correspond to each of the plurality of regions divided in the image dividing step.

A medical image processing method according to a third aspect of the present invention includes: a three-dimensional model estimating step for estimating a three-dimensional model of an object based on a two-dimensional image of an image of the object which is inputted from a medical image pickup apparatus; an image dividing step for dividing the two-dimensional image into a plurality of regions each of which includes at least one or more pixels; an image position detecting step for detecting a positional relationship between the positions of each of the plurality of regions on the two-dimensional image and a predetermined position on the two-dimensional image; and a lesion detection reference setting step for setting a lesion detection reference for detecting a locally protruding lesion in the regions of the three-dimensional model that correspond to each of the plurality of regions, based on the positional relationship detected by the image position detecting step.

DETAILED DESCRIPTION OF THE PREFERRED EMBODIMENT(S)

Now, with reference to the drawings, embodiments of the present invention will be explained below.

First Embodiment

Figure 1:
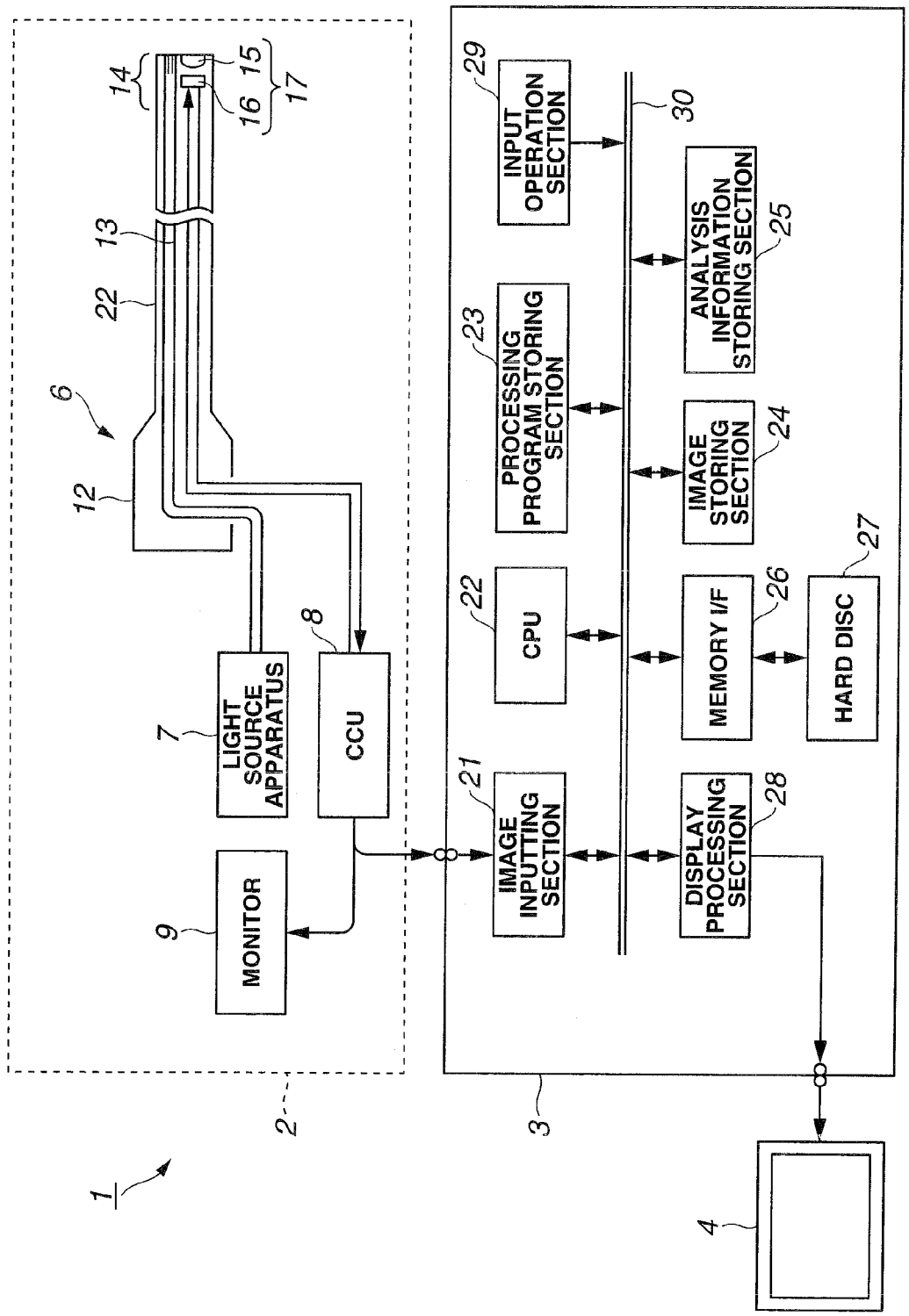
FIG. 1 is a diagram showing an example of the entire configuration of an endoscope system to which a medical image processing apparatus according to an embodiment of the present invention is used.
Figure 2:
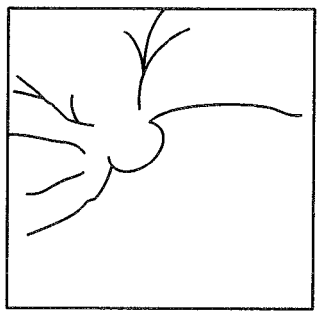
FIG. 2 is a diagram showing an example of a two-dimensional image of an object which is picked up by the endoscope system of FIG. 1.
Figure 3:
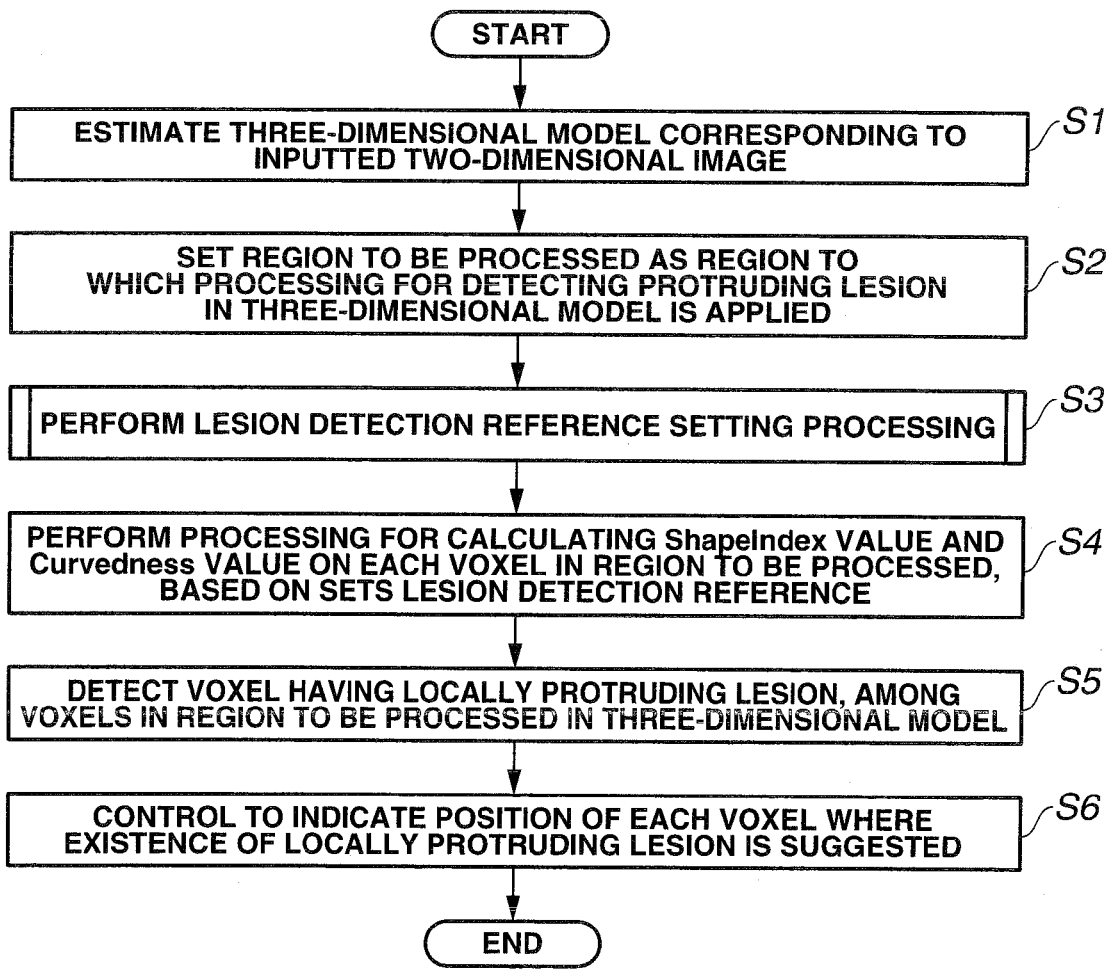
FIG. 3 is a flowchart showing a procedure of a processing performed by the medical image processing apparatus of FIG. 1 in a first embodiment.
Figure 4:
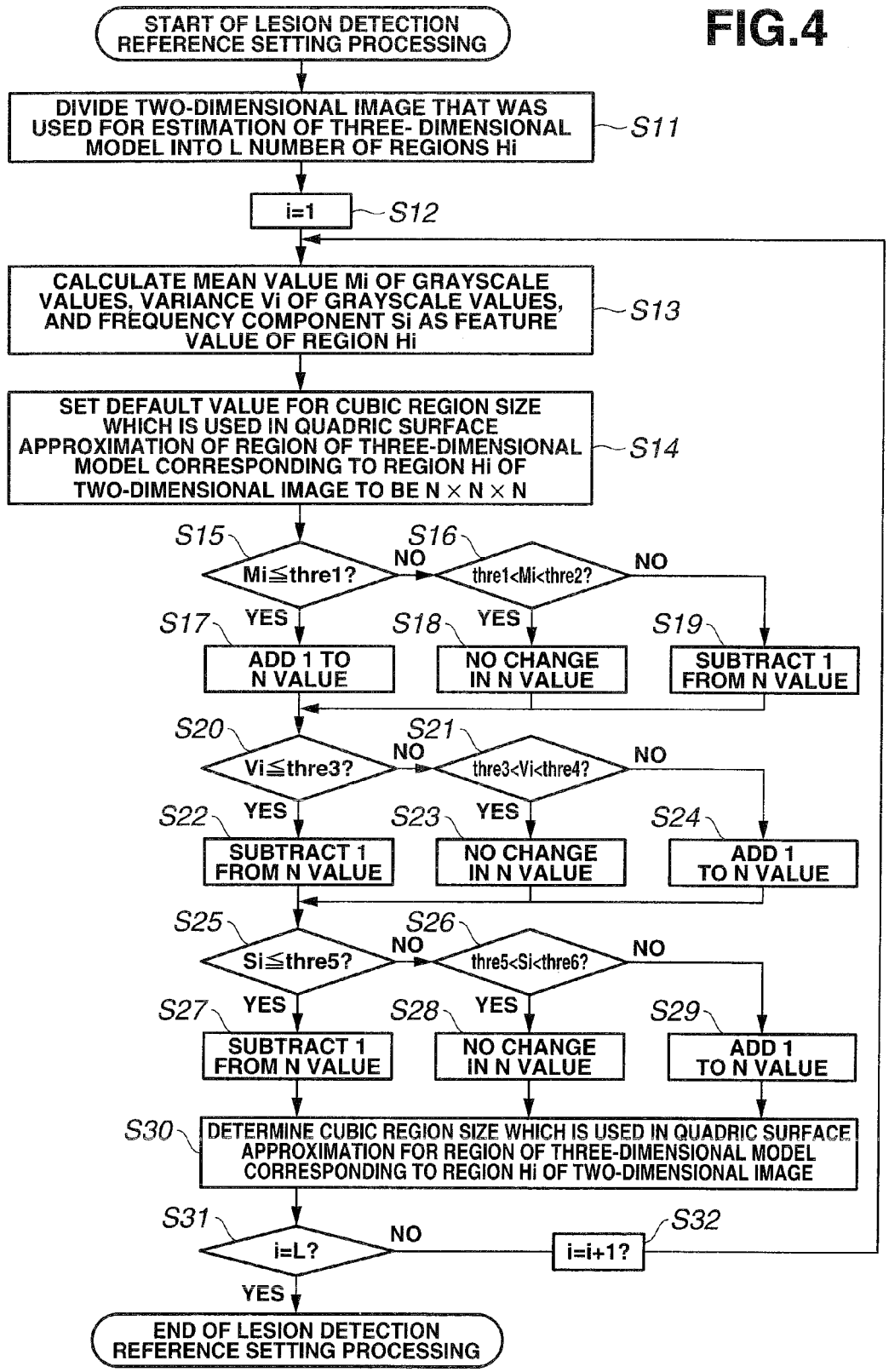
FIG. 4 is a flowchart showing an example of a processing performed in the first embodiment as the lesion detection reference setting processing of FIG. 3.
Figure 5:
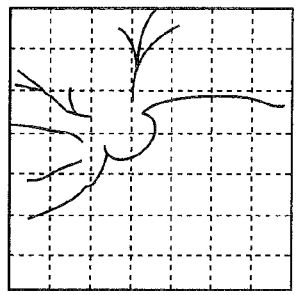
FIG. 5 is a diagram showing an example of a processing result when the two-dimensional image shown in FIG. 2 is divided into a plurality of regions.
Figure 6:
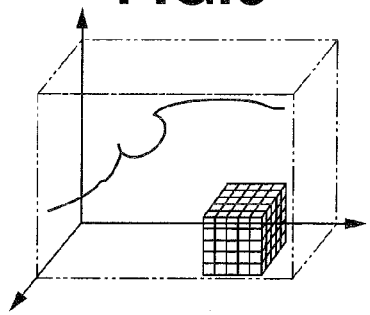
FIG. 6 is a diagram showing a condition example where the lesion detection reference set by each processing of FIG. 4 is applied to the three-dimensional model estimated by the medical image processing apparatus of FIG. 1.
Figure 7:
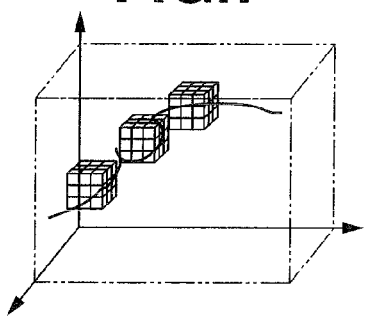
FIG. 7 is a diagram showing a condition example different from that of FIG. 6 where the lesion detection reference set by each processing of FIG. 4 is applied to the three-dimensional model estimated by the medical image processing apparatus of FIG. 1.

FIGS. 1 to 7 relate to a first embodiment of the present invention. FIG. 1 is a diagram showing an example of the entire configuration of an endoscope system to which a medical image processing apparatus according to an embodiment of the present invention is used. FIG. 2 is a diagram showing an example of a two-dimensional image of an object which is picked up by the endoscope system of FIG. 1. FIG. 3 is a flowchart showing a procedure of a processing performed by the medical image processing apparatus of FIG. 1 in a first embodiment. FIG. 4 is a flowchart showing an example of a processing performed in the first embodiment as the lesion detection reference setting processing of FIG. 3. FIG. 5 is a diagram showing an example of a processing result when the two-dimensional image shown in FIG. 2 is divided into a plurality of regions. FIG. 6 is a diagram showing a condition example where the lesion detection reference set by each processing of FIG. 4 is applied to the three-dimensional model estimated by the medical image processing apparatus of FIG. 1. FIG. 7 is a diagram showing a condition example different from that of FIG. 6 where the lesion detection reference set by each processing of FIG. 4 is applied to the three-dimensional model estimated by the medical image processing apparatus of FIG. 1.

An endoscope system 1 is, as shown in FIG. 1, configured with the main part, including: a medical observation apparatus 2 that picks up an image of an object and also outputs a two-dimensional image of the object image; a medical image processing apparatus 3 that is constituted with a personal computer and the like and processes the video signal of the two-dimensional image outputted from the medical observation apparatus 2, and also outputs the video signal after the image processing as an image signal; and a monitor 4 that displays an image based on the image signal outputted from the medical image processing apparatus 3.

The medical observation apparatus 2 is configured with the main part, including: an endoscope 6 that is inserted into a body cavity of a subject and picks up an image of an object such as living tissue in the body cavity to output the image as an image pickup signal; a light source apparatus 7 for supplying illumination light for illuminating the object the image of which is picked up by the endoscope 6; a camera control unit (hereinafter, simply referred to as CCU) 8 which variously controls the endoscope 6, and also processes the image pickup signal outputted from endoscope 6 to output as a video signal of the two-dimensional image; and a monitor 9 that displays the object image picked up by the endoscope 6, based on the video signal of the two-dimensional image outputted from the CCU 8.

The endoscope 6 is configured with an insertion portion 11 which is inserted into a body cavity and an operation portion 12 which is provided on the proximal end side of the insertion portion 11. The insertion portion 11 includes a light guide 13 provided therethrough from the proximal end side of the insertion portion 11 to a distal end portion 14 at the distal end side of the insertion portion 11 for transmitting illumination light which is supplied from the light source apparatus 7.

The light guide 13 has a distal end portion disposed at the distal end portion 14 of the endoscope 6, and a rear end portion connected to the light source apparatus 7. The configuration of the light guide 13 allows the illumination light supplied from the light source apparatus 7 to be transmitted through the light guide 13 to go out from an illumination window (not shown) provided on the distal end face of the distal end portion 14 of the insertion portion 11. The illumination light from the illumination window (not shown) illuminates living tissue and the like as an object.

The endoscope 6 has a distal end portion 14 provided with an image pickup section 17 which includes an objective optical system 15 mounted to an observation window (not shown) adjacent to the illumination window (not shown), and an image pickup device 16 that is disposed at the image-forming position of the objective optical system 15 and is constituted with a CCD (charge coupled device) and the like. The configuration allows the object image focused by the objective optical system 15 to be picked up by the image pickup device 16 and outputted as an image pickup signal.

The image pickup device 16 is connected to the CCU 8 via a signal line. The image pickup device 16 is driven based on the drive signal outputted from the CCU 8, and also outputs an image pickup signal corresponding to a picked-up object image.

The image pickup signal inputted to the CCU 8 is processed in a signal processing circuit (not shown) provided in the CCU 8, so as to be converted and outputted as a video signal of the two-dimensional image. The video signal of the two-dimensional image outputted from the CCU 8 is outputted to the monitor 9 and the medical image processing apparatus 3. As a result, the monitor 9 displays an object image based on a video signal outputted from the CCU 8 as a two-dimensional image.

The medical image processing apparatus 3 includes: an image inputting section 21 for A/D conversion of the video signal of a two-dimensional image outputted from the medical observation apparatus 2, and outputting of the converted signal; a CPU 22 as a central processing unit for image processing of the video signal outputted from the image inputting section 21; a processing program storing section 23 that has programs for image processing written therein; an image storing section 24 for storing video signals and the like outputted from the image inputting section 21; and an analysis information storing section 25 for storing operation results and the like in the image processings executed by the CPU 22.

The medical image processing apparatus 3 includes: a memory interface 26; a hard disc 27 as a memory for storing image data and the like as image processing result by the CPU 22 through the memory interface 26; a display processing section 28 which performs a display processing for displaying the image data on the monitor 4 based on the image data as the image processing result by the CPU 22, and outputs the image data after the image processing as an image signal; an input operation section 29 which is constituted with a keyboard and the like to which a user is able to input the parameters of the image processing performed by the CPU 22 and the operation instructions to the medical image processing apparatus 3. The monitor 4 displays an image based on the image signal outputted from the display processing section 28.

The image inputting section 21, the CPU 22, the processing program storing section 23, the image storing section 24, the analysis information storing section 25, the memory interface 26, the display processing section 28, and the input operation section 29 in the medical image processing apparatus 3 are connected to each other via a data bus 30.

Next, the operations of the endoscope system 1 will be explained below.

First, a user turns on power of each section of the endoscope system 1, and then inserts the insertion portion 11 of the endoscope 6 into a body cavity of a subject.

After the insertion of insertion portion 11 into the body cavity of the subject, for example, an image of object such as living tissue in the body cavity is picked up by the image pickup section 17 provided at the distal end portion 14. The image picked up by the image pickup section 17 is outputted to the CCU 8 as an image pickup signal.

The CCU 8 performs a processing of the image pickup signal outputted from the image pickup device 16 of the image pickup section 17 in a signal processing circuit (not shown), so as to convert the image pickup signal into a video signal of a two-dimensional image, and outputs the signal. The monitor 9 displays the object image picked up by the image pickup section 17 based on the video signal outputted from the CCU 8 as a two-dimensional image such as that shown in FIG. 2. Also, the CCU 8 outputs the video signal of the two-dimensional image which is obtained by the processing of the image pickup signal outputted from the image pickup device 16 of the image pickup section 17, to the medical image processing apparatus 3.

The video signal of the two-dimensional image outputted to the medical image processing apparatus 3 is subjected to A/D conversion in the image inputting section 21, to be inputted to the CPU 22.

The CPU 22 as a three-dimensional model estimating section performs a processing of geometrical transformation and the like based on the luminance information of the two-dimensional image onto the two-dimensional image outputted from the image inputting section 21 using the Shape From Shading method for example, so as to estimate a three-dimensional model corresponding to the two-dimensional image (Step S1 of FIG. 3).

Next, the CPU 22 detects the change of colors in the two-dimensional image outputted from the image inputting section 21, and the change of protruded state in the three-dimensional model estimated by the processing at Step S1, so as to set the region to be processed as a region to which a processing for detecting a protruding lesion in the three-dimensional model is applied (Step S2 of FIG. 3). Specifically, the CPU 22 separates the two-dimensional image outputted from the image inputting section 21 into plane images of an R (red) image, a G (green) image and a B (bleu) image for example, and then detects the change of protruded state based on the data of the three-dimensional model data estimated according to the R image, and also detects the change of colors based on the chromaticity of the R image and the G image. Then, based on the detection result of the change of protruded state and the detection result of the change of colors, the CPU 22 sets the region from which both of the change of protruded state and the change of colors are detected to be the region to be processed. Hereinafter, for the simplification of explanation, the following explanation is based on the assumption that the entire region of the three-dimensional model which is estimated according to the two-dimensional image shown in FIG. 2 by the processing shown at Step S2 of FIG. 3 is set to be the region to be processed.

Then, the CPU 22 performs a lesion detection reference setting processing which will be described below, as a processing for setting a lesion detection reference that is used to detect a locally protruding lesion such as a polyp in a three-dimensional model (Step S3 of FIG. 2).

The CPU 22 as an image dividing section first divides the two-dimensional image shown in FIG. 2 which was used in the estimation of a three-dimensional model into the L number ($2 \leq L$) of regions Hi ($1 \leq i \leq L$) each of which includes at least one or more pixels, as shown in FIG. 5, as the lesion detection reference setting processing (Step S11 of FIG. 4).

Next, the CPU 22 as a feature value calculation section sets a variable i=1 (Step S12 of FIG. 4), and then calculates the mean value Mi of grayscale value of each pixel included in the region Hi, the variance Vi of grayscale value of each pixel included in the region Hi, and the frequency component Si of the region Hi, as feature values of the region Hi (Step S13 of FIG. 4). The frequency component Si of the region Hi is for example assumed to be obtained by performing a filtering processing on the region Hi using a Sobel filter, laplacian filter or the like.

Then, the CPU 22 sets the default value for a cubic region size which is used in quadric surface approximation of the region of a three-dimensional model corresponding to the region Hi of the two-dimensional image to be N×N×N (Step S14 of FIG. 4).

The CPU 22 as a lesion detection reference setting section performs a comparison processing based on the mean value Mi of the grayscale value of the region Hi which is calculated by the processing shown at Step S13 of FIG. 4. Then, the CPU 22 adds 1 to the N value (Step S17 of FIG. 4) when the CPU 22 detects that the mean grayscale value Mi is equal to o less than a threshold thre1 (Step S15 of FIG. 4), and then performs the processing at Step S20 of FIG. 4 which will be described later. Also, the CPU 22 does not change the N value (Step S18 of FIG. 4) when the CPU 22 detects that the mean grayscale value Mi is larger than the threshold thre1 and less than a threshold thre2 (Step S16 of FIG. 4), and then performs the processing at Step S20 of FIG. 4 which will be described later. Moreover, the CPU 22 subtracts 1 from the N value (Step S19 of FIG. 4) when the CPU 22 detects that the mean grayscale value Mi is larger than the threshold thre2 (Step S16 of FIG. 4), and then performs the processing at Step S20 of FIG. 4 which will be described later.

That is, a brighter part (bright region) of a two-dimensional image has the mean grayscale value Mi of the region Hi which is a relatively large value. As a result, the region of a three-dimensional model corresponding to the bright region of the two-dimensional image has dense data. Thus, the above described respective processings shown at Step S15 of FIG. 4, at Step S16 of FIG. 4, and at Step S19 of FIG. 4 are performed, which decreases the cubic region size which is used in quadric surface approximation for the region of the estimated three-dimensional model that contains dense data.

Also, the mean grayscale value Mi of region Hi is a relatively small value in a darker part (dark region) of a two-dimensional image. As a result, the region of a three-dimensional model corresponding to the dark region of the two-dimensional image has sparse data. Thus, the above described respective processings shown at Step S15 of FIG. 4 and at Step S17 of FIG. 4 are performed, which increases the cubic region size which is used in quadric surface approximation for the region of the estimated three-dimensional model that contains sparse data.

The CPU 22 performs a comparison processing based on the variance Vi of the grayscale values in the region Hi which was calculated at the processing shown at Step S13 of FIG. 4. When the CPU 22 detects that the variance Vi of the grayscale value is equal to or less than a threshold thre3 (Step S20 of FIG. 4), the CPU 22 subtracts 1 from the N value (Step S22 of FIG. 4) and then performs the processing at Step S25 of FIG. 4 which will be described later. Also, when the CPU 22 detects that the variance Vi of the grayscale value is larger than the threshold thre3 and equal to or less than a threshold thre4 (Step S21 of FIG. 4), without changing the N value (Step S23 of FIG. 4), the CPU 22 performs the processing at Step S25 of FIG. 4 which will be described later. Furthermore, when the CPU 22 detects that the variance Vi of the grayscale value is larger than a threshold thre4 (Step S21 of FIG. 4), the CPU 22 adds 1 to the N value (Step S24 of FIG. 4), and then performs the processing at Step S25 of FIG. 4 which will be described later.

That is, a part of a two-dimensional image including a large number of edges has the variance Vi of the grayscale values in the region Hi which is a relatively large value. As a result, the region of a three-dimensional model corresponding to the region of the two-dimensional image having a large number of edges contains dense data. Thus, the above described respective processings shown at Step S20 of FIG. 4 and at Step S22 of FIG. 4 are performed, which decreases the cubic region size which is used in quadric surface approximation for the region of the estimated three-dimensional model that contains dense data.

Also, a part of a two-dimensional image including no edges (or a small number of edges) has the variance Vi of the grayscale values in the region Hi which is a relatively small value. As a result, the region of a three-dimensional model corresponding to the region of the two-dimensional image having no edges (or a small number of edges) contains sparse data. Thus, the above described respective processings shown at Step S20 of FIG. 4, at Step 21 of FIG. 4, and at Step S24 of FIG. 4 are performed, which increases the cubic region size which is used in quadric surface approximation for the region of the estimated three-dimensional model that contains sparse data.

The CPU 22 performs a comparison processing based on the frequency component Si of the region Hi which was calculated at the processing shown at Step S13 of FIG. 4. When the CPU 22 detects that the frequency component Si is equal to or less than a threshold thre5 (Step S25 of FIG. 4), the CPU 22 subtracts 1 from the N value (Step S27 of FIG. 4) and then performs the processing at Step S30 of FIG. 4 which will be explained later. Also, when the CPU 22 detects that the frequency component Si is larger than the threshold thre5 and equal to or less than a threshold thre6 (Step S26 of FIG. 4), without changing the N value (Step S28 of FIG. 4), the CPU 22 performs the processing at Step S30 of FIG. 4 which will be described later. Furthermore, when the CPU 22 detects that the frequency component Si is larger than a threshold thre6 (Step S26 of FIG. 4), the CPU 22 adds 1 to the N value (Step S29 of FIG. 4), and then performs the processing at Step S30 of FIG. 4 which will be described later.

That is, a part of a two-dimensional image having (a large number of) edges has a frequency component Si of the region Hi which is a relatively large value. As a result, the region of a three-dimensional model corresponding to the region of the two-dimensional image having (a large number of) edges contains dense data. Thus, the above described respective processings shown at Step S25 of FIG. 4 and at Step S27 of FIG. 4 are performed, which decreases the cubic region size which is used in quadric surface approximation for the region of the estimated three-dimensional model that contains dense data.

Also, a part of a two-dimensional image having no edges (or a small number of edges) has a frequency component Si of the region Hi which is a relatively small value. As a result, the region of a three-dimensional model corresponding to the region of the two-dimensional image having no edges (or a small number of edges) contains sparse data. Thus, the above described respective processings shown at Step S25 of FIG. 4, at Step S26 of FIG. 4, and at Step S29 of FIG. 4 are performed, which increases the cubic region size which is used in quadric surface approximation for the region of the estimated three-dimensional model that contains sparse data.

The CPU 22 determines the cubic region size which is used in quadric surface approximation for the region of a three-dimensional model corresponding to the region Hi of the two-dimensional image as the size changed by performing the above described processings from Step S15 to Step S29 of FIG. 4 (Step S30 of FIG. 4). Then, the CPU 22 sets the cubic region size determined at Step S30 of FIG. 4 as the lesion detection reference for the region of a three-dimensional model corresponding to the region Hi of the two-dimensional image.

Then, CPU 22 determines if the above described processings were performed for all of the L number of regions Hi or not, that is if the variable i=L or not. When the CPU 22 detects that the variable i is not equal to L (Step S31 of FIG. 4), the CPU 22 adds 1 to the variable i (Step S32 of FIG. 4), and again performs the above described processings from Step S13 to Step S31 of FIG. 4. When the CPU 22 detects that the variable i is equal to L (Step S31 of FIG. 4), the CPU 22 ends the lesion detection reference setting processing.

The CPU 22 performs the processing for calculating a ShapeIndex value and a Curvedness value of each voxel in the region to be processed which was set at Step S2 of FIG. 3, based on the lesion detection reference set in the lesion detection reference setting processing shown in FIG. 4 (Step S4 of FIG. 3).

Now, the processing at Step S4 of FIG. 3 of the present embodiment will be described below in detail.

The CPU 22 performs quadric surface approximation for each region of the three-dimensional model corresponding to each region Hi of the two-dimensional image, based on the cubic region size as the lesion detection reference which was set in the lesion detection reference setting processing shown in FIG. 4.

The region of the three-dimensional model corresponding to the region that is a dark region and has no edge in the two-dimensional image shown in FIG. 2 contains sparse data which is useful in the detection of a locally protruding lesion. Therefore, the CPU 22 performs quadric surface approximation for the region of a three-dimensional model containing sparse data, using a cubic region having a 5×5×5 size as the lesion detection reference for example, as shown in FIG. 6.

Also, the region of the three-dimensional model corresponding to the region that lies on the boundary between the bright region and the dark region of the two-dimensional image shown in FIG. 2 and has edges contains dense data which is useful in the detection of a locally protruding lesion. Therefore, the CPU 22 performs quadric surface approximation for the region of a three-dimensional model containing dense data, using a cubic region having a 3×3×3 size as the lesion detection reference for example, as shown in FIG. 7.

The CPU 22 calculates a local partial differential coefficient for each region of the three-dimensional model based on the result of the above described quadric surface approximation, and also based on the local partial differential coefficient, calculates a ShapeIndex value that represents the unevenness of each voxel in the three-dimensional model and a Curvedness value that represents the curvature of each voxel in the three-dimensional model. The method for calculating ShapeIndex value and Curvedness value based on local partial differential coefficient may be the one similar to that described in US Patent Application Publication No. 20030223627 for example. Thus, the method for calculating ShapeIndex value and Curvedness value will not be described in detail in the present embodiment.

Then, the CPU 22 performs a threshold processing and the like based on the ShapeIndex value and the Curvedness value calculated in the processing at Step S4 of FIG. 3, so as to detect the voxel having a locally protruding lesion among the voxels in the region to be processed which was set at Step S2 of FIG. 3 (Step S5 of FIG. 3).

The CPU 22 performs a control onto the display processing section 28 to superimpose text string or color on the three-dimensional model (Step S6 of FIG. 3), as a control to indicate the position of each voxel where the existence of a locally protruding lesion is suggested, based on the detection result of the processing at Step S5 of FIG. 3, and then the CPU 22 ends a series of the above described processings.

As a result, the monitor 4 displays a three-dimensional model of an object in which the position of a locally protruding portion such as a polyp is easily recognizable by a user.

The medical image processing apparatus 3 of the present embodiment performs a series of the above described processings shown in FIG. 3 and FIG. 4, so as to improve the accuracy in the detection of a locally protruding lesion in a three-dimensional model as compared to the prior art.

Second Embodiment

Figure 8:
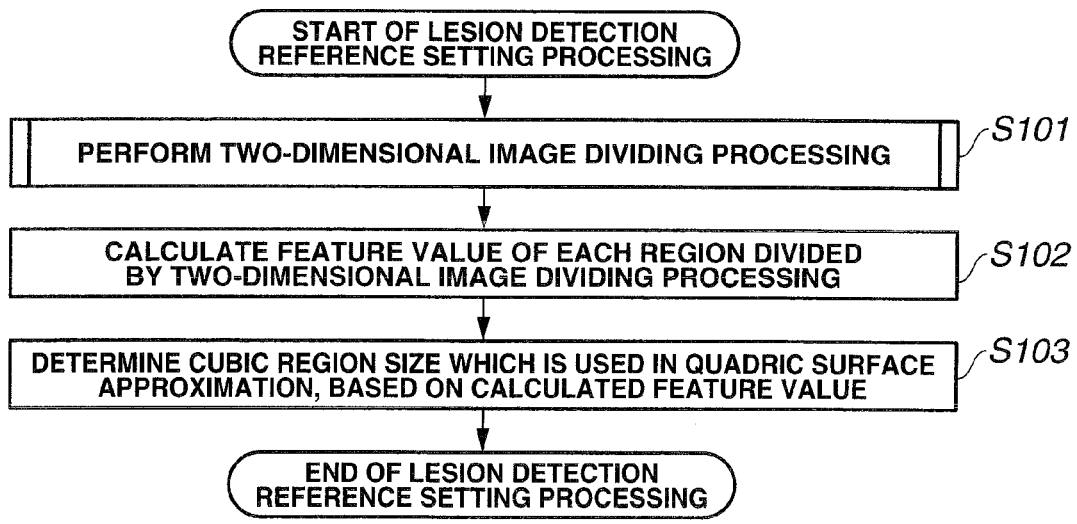
FIG. 8 is a flowchart showing an example of a processing performed in a second embodiment as the lesion detection reference setting processing in FIG. 3.
Figure 9:
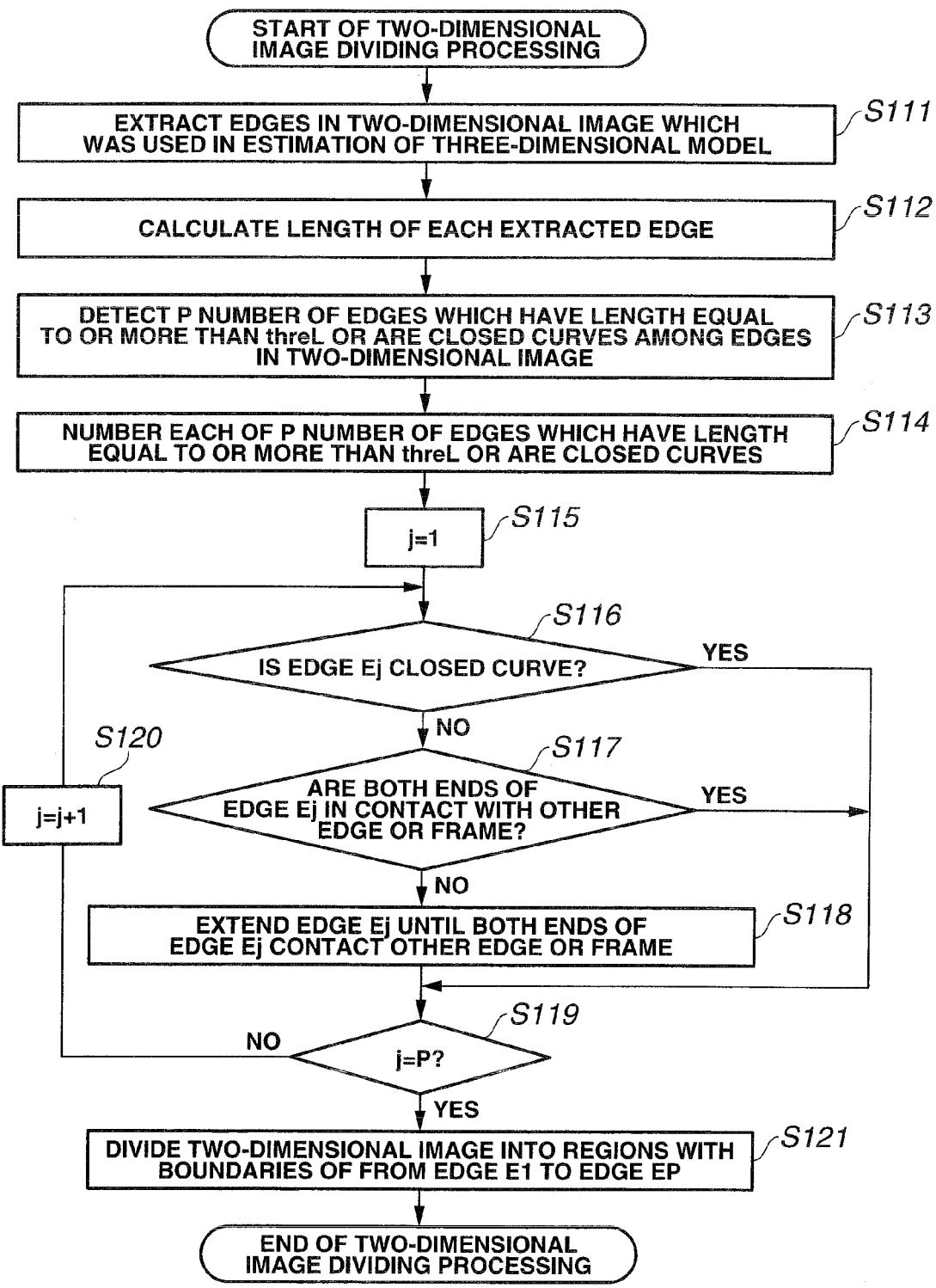
FIG. 9 is a flowchart showing an example of the two-dimensional image division processing of FIG. 8.
Figure 10:
FIG. 10 is a diagram showing an example of a two-dimensional image which is used in the processing of FIG. 9.
Figure 11:
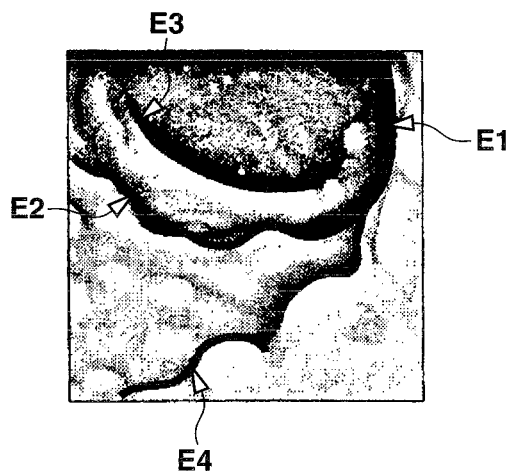
FIG. 11 is a diagram showing an example of an edge detected by the processing of FIG. 9.
Figure 12:
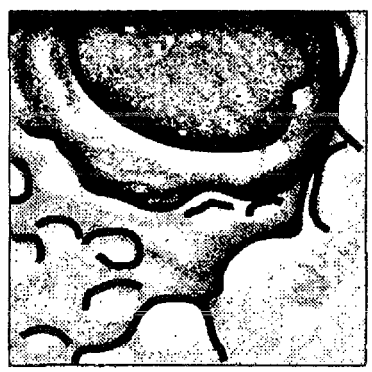
FIG. 12 is a diagram showing an example, different from that of FIG. 11, of an edge detected by the processing of FIG. 9.
Figure 13:
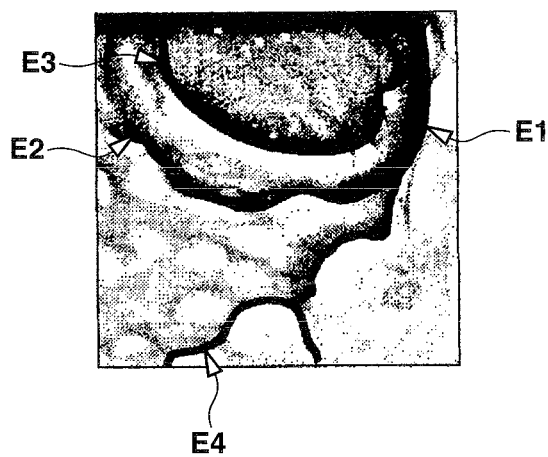
FIG. 13 is a diagram showing an extended condition of each edge of FIG. 11 based on the edges of FIG. 12.
Figure 14:
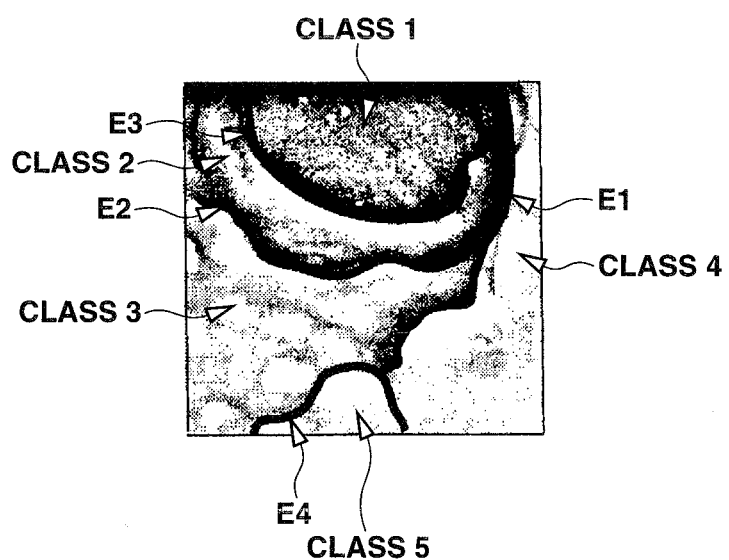
FIG. 14 is a diagram showing a processing result of the region division of the two-dimensional image shown in FIG. 10 by the processing of FIG. 9.
Figure 15:
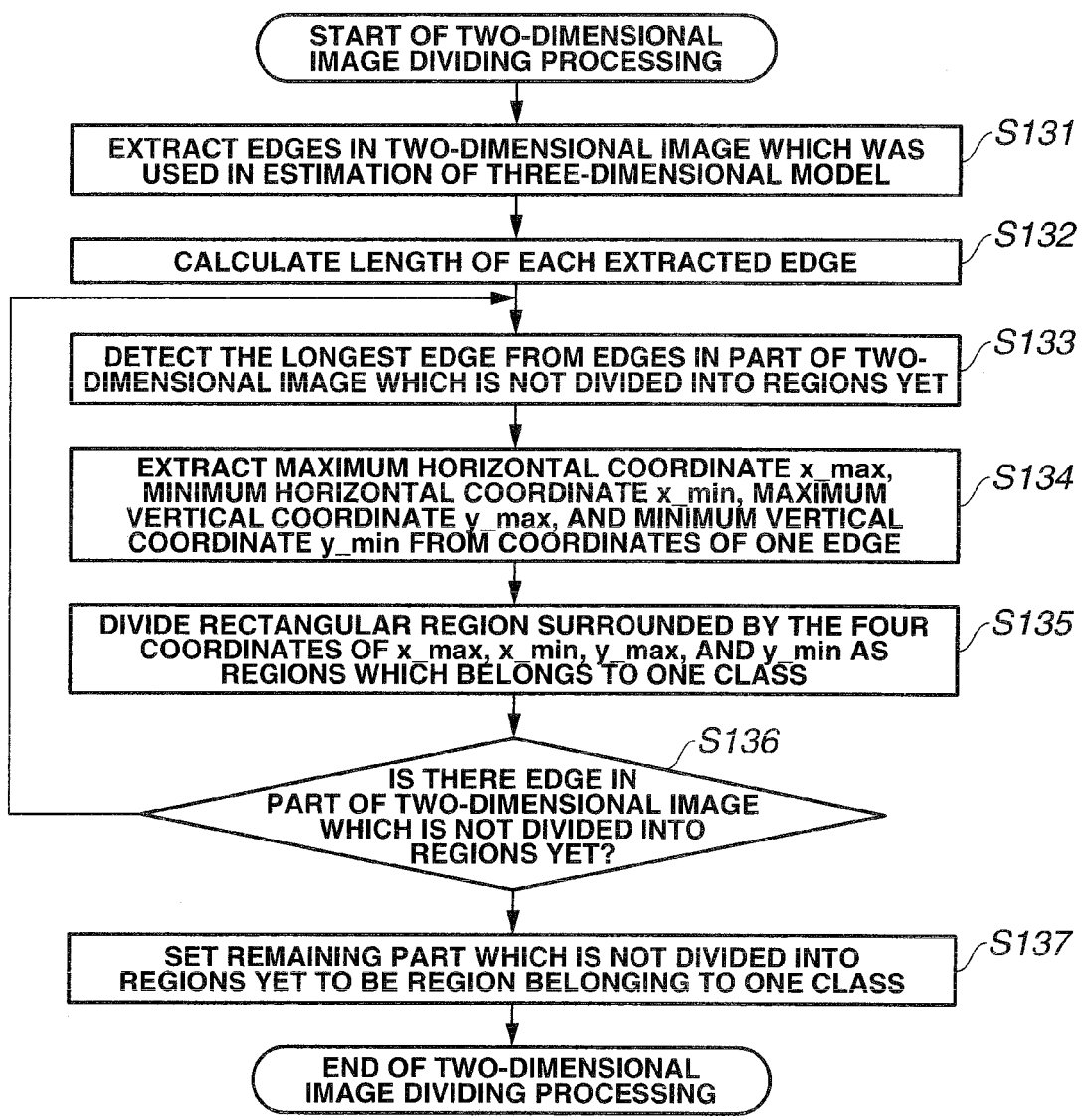
FIG. 15 is a flowchart showing an example, different from that of FIG. 9, of the two-dimensional image division processing shown in FIG. 8.
Figure 16:
FIG. 16 is a diagram showing an example of the edge detected by the processing of FIG. 15.
Figure 17:
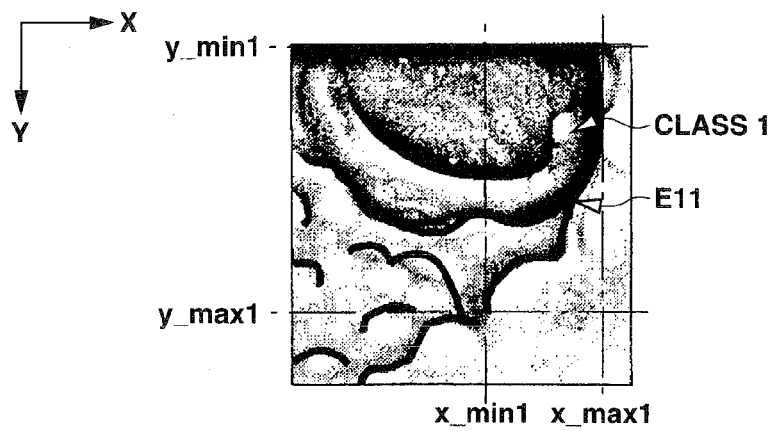
FIG. 17 is a diagram showing an example of the condition where a part of the two-dimensional image of FIG. 10 is divided into regions by the processing of FIG. 15.
Figure 18:
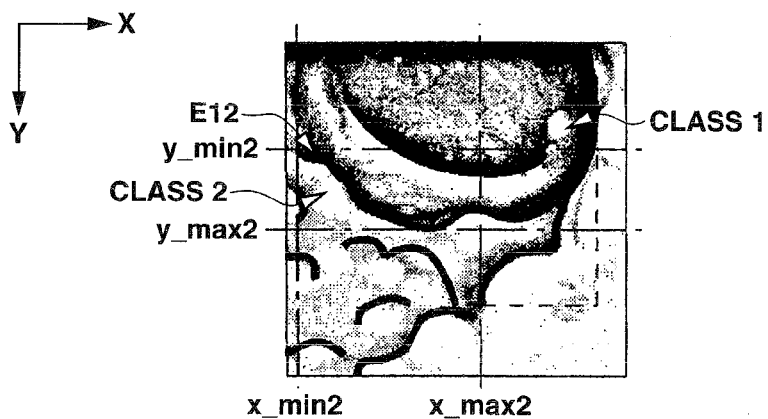
FIG. 18 is a diagram showing an example, different from that of FIG. 17, of the condition where a part of the two-dimensional image of FIG. 10 is divided into regions by the processing of FIG. 15.

FIGS. 8 to 22 relate to a second embodiment of the present invention. FIG. 8 is a flowchart showing an example of a processing performed in a second embodiment as the lesion detection reference setting processing in FIG. 3. FIG. 9 is a flowchart showing an example of the two-dimensional image division processing of FIG. 8. FIG. 10 is a diagram showing an example of a two-dimensional image which is used in the processing of FIG. 9. FIG. 11 is a diagram showing an example of an edge detected by the processing of FIG. 9. FIG. 12 is a diagram showing an example, different from that of FIG. 11, of an edge detected by the processing of FIG. 9. FIG. 13 is a diagram showing an extended condition of each edge of FIG. 11 based on the edges of FIG. 12. FIG. 14 is a diagram showing a processing result of the region division of the two-dimensional image shown in FIG. 10 by the processing of FIG. 9. FIG. 15 is a flowchart showing an example, different from that of FIG. 9, of the two-dimensional image division processing shown in FIG. 8. FIG. 16 is a diagram showing an example of the edge detected by the processing of FIG. 15. FIG. 17 is a diagram showing an example of the condition where a part of the two-dimensional image of FIG. 10 is divided into regions by the processing of FIG. 15. FIG. 18 is a diagram showing an example, different from that of FIG. 17, of the condition where a part of the two-dimensional image of FIG. 10 is divided into regions by the processing of FIG. 15.

Figure 19:
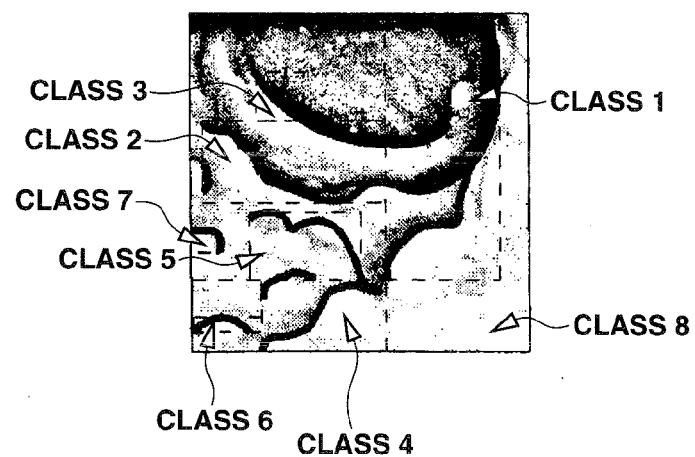
FIG. 19 is a diagram showing a processing result of the region division of the two-dimensional image shown in FIG. 10 by the processing of FIG. 15.
Figure 20:
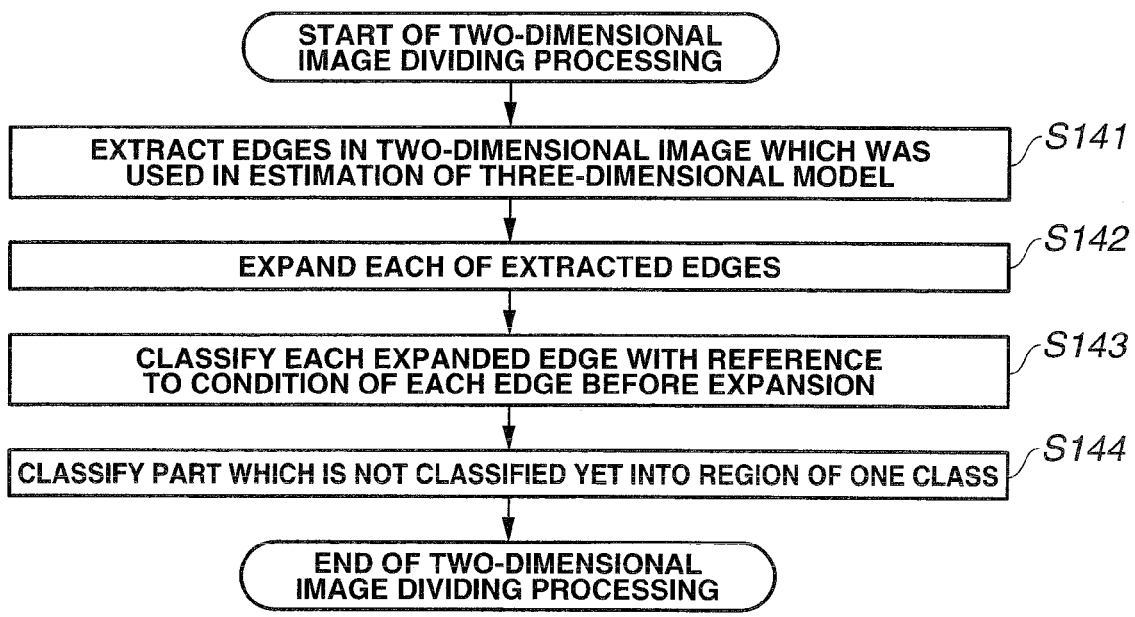
FIG. 20 is a flowchart showing an example, different from those of FIGS. 9 and 15, of the two-dimensional image division processing of FIG. 8.
Figure 21:
FIG. 21 is a diagram showing an example of the processing result when the line thickness of each edge shown in FIG. 16 is increased by the processing of FIG. 20.
Figure 22:
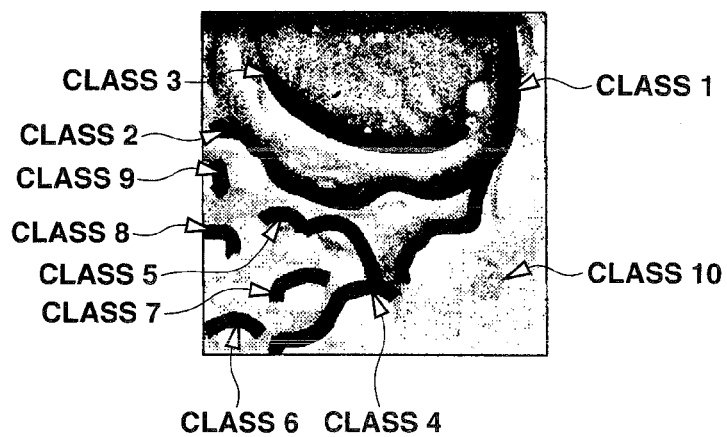
FIG. 22 is a diagram showing the processing result when the two-dimensional image of FIG. 10 is divided into regions by the processing of FIG. 20.

Also, FIG. 19 is a diagram showing a processing result of the region division of the two-dimensional image shown in FIG. 10 by the processing of FIG. 15. FIG. 20 is a flowchart showing an example, different from those of FIGS. 9 and 15, of the two-dimensional image division processing of FIG. 8. FIG. 21 is a diagram showing an example of the processing result when the line thickness of each edge shown in FIG. 16 is increased by the processing of FIG. 20. FIG. 22 is a diagram showing the processing result when the two-dimensional image of FIG. 10 is divided into regions by the processing of FIG. 20.

The part having the same configuration as that of the first embodiment will not be explained below. Also, the components similar to those of the first embodiment are designated with the same numeral references, and will not be explained below. The endoscope system 1 used in the present embodiment has the same configuration as that of the first embodiment.

Next, the image processing operation by the medical image processing apparatus 3 will be explained below.

The CPU 22 performs the processings similar to those at Step S1 and Step S2 of FIG. 3 which were already explained in the first embodiment, and then performs a lesion detection reference setting processing (Step S3 of FIG. 3) which will be explained below, as a processing for setting the lesion detection reference to be used in the detection of a locally protruding lesion such as a polyp in a three-dimensional model.

The CPU 22 first performs a two-dimensional image division processing for dividing the two-dimensional image shown in FIG. 10, for example, which was used in the estimation of the three-dimensional model as a lesion detection reference setting processing, which will be explained below (Step S101 of FIG. 8).

In the two-dimensional image division processing, the CPU 22 as an image information extracting section first extracts edges of the two-dimensional image which are the image information according to the grayscale of each pixel included in the two-dimensional image used in the estimation of the three-dimensional model, by a filtering processing (Step S111 of FIG. 9), and also calculates the length of each extracted edge (Step S112 of FIG. 9).

Next, the CPU 22 detects a P number of edges that have a length of a threshold threL or more or are closed curves among the edges in the two-dimensional image (Step S113 of FIG. 9), and also gives number the edges such as E1, E2, . . . , Ej, ($1 \leq j \leq P$) in descending order of length (Step S114 of FIG. 9). Specifically, the above described processing from Step S111 to Step S114 of FIG. 9 are performed, so that four edges from an edge E1 to an edge E4 are detected as shown in FIG. 11 for example, as edges to be mainly used in the subsequent processings, among the edges in the two-dimensional image shown in FIG. 10.

Then, the CPU 22 sets a variable j=1 (Step S115 of FIG. 9), and then determines if the edge Ej is a closed curve or not. Then, when the CPU 22 detects that the edge Ej is a closed curve (Step S116 of FIG. 9), the CPU 22 performs the processing shown at Step S119 of FIG. 9 which will be explained later. When the CPU 22 detects that the edge Ej is not a closed curve (Step S116 of FIG. 9), the CPU 22 determines if both ends of the edge Ej are in contact with other edge or a frame (edge portion of the image) or not.

When the CPU 22 detects that both ends of the edge Ej are in contact with other edge or the frame (Step S117 of FIG. 9), the CPU 22 performs the processing shown at Step S119 of FIG. 9 which will be explained later. When the CPU 22 detects that at least one of the ends of the edge Ej is in contact with none of other edge and the frame (Step S117 of FIG. 9), the CPU 22 extends the edge Ej until both ends of the edge Ej contacts one of other edge and the frame (Step S118 of FIG. 9).

Now, one example of the processing at Step S118 of FIG. 9 will be explained below in detail.

The CPU 22 extracts the edges in the two-dimensional image by performing a filtering processing with a filter that has a low threshold to a frequency component as compared to the filter used in the processing at Step S111 of FIG. 9 for example. Specifically, the CPU 22 extracts each of the edges shown in FIG. 12 as the edges in the two-dimensional image shown in FIG. 10 for example by performing the filtering processing.

Then, the CPU 22 extends the edge Ej at one end of both ends of the edge Ej which is in contact with none of other edge and the frame, with reference to the edges extracted in the filtering processing. This processing allows both ends of the edge Ej to be in contact with one of the other edge or the frame. Specifically, the CPU 22 obtains the processing result as that shown in FIG. 13 for example, by extending each of the edges of the edge E1 to the edge E4 shown in FIG. 11, with reference to the edges shown in FIG. 12.

Furthermore, the CPU 22 determines if the above described processings were performed on all of the P number of edges Ej or not, that is the variable j=P or not. When the CPU 22 detects that the variable j is not equal to P (Step S119 of FIG. 9), the CPU 22 adds 1 to the variable j (Step S120 of FIG. 9), and then again performs the above described processings from Step S116 to Step S119 of FIG. 9. When the CPU 22 as an image dividing section detects that the variable j is equal to P (Step S119 of FIG. 9), the CPU 22 divides the two-dimensional image into regions with boundaries of from the edge E1 to the edge EP (Step S121 of FIG. 9), and then ends the two-dimensional image division processing. Specifically, the CPU 22 divides the two-dimensional image shown in FIG. 10 into five regions from class 1 to class 5 for example as shown in FIG. 14 with the boundaries of the edges E1 to E4 which were extended in the processing at Step S118 of FIG. 9, by the above described two-dimensional image division processing.

Then, the CPU 22 calculates feature values such as the mean grayscale value for each of the regions divided in the two-dimensional image division processing (Step S102 of FIG. 8), and based on the calculated feature value, determines the size of a cubic region which is used in quadric surface approximation (and the calculation of ShapeIndex value and Curvedness value) in regions of the three-dimensional model corresponding to each of the regions divided in the two-dimensional image division processing (Step S103 of FIG. 8), and then ends the lesion detection reference setting processing.

That is, the CPU 22 performs the above described lesion detection reference setting processing to determine the size of a cubic region which is used in quadric surface approximation (and the calculation of ShapeIndex value and Curvedness value) in regions of the three-dimensional model corresponding to each of the regions divided in the two-dimensional image division processing. Specifically, when the two-dimensional image division processing is used as the processing shown in FIG. 9, the regions of the three-dimensional model corresponding to the regions of classes 1 and 2 for example among the regions of classes 1 to 5 in the two-dimensional image shown in FIG. 14 are detected as the regions containing sparse data which is useful in detecting of a locally protruding lesion. Thus, the CPU 22 uses a cubic region of a relatively large size as a lesion detection reference for the regions of the three-dimensional model corresponding to the regions at classes 1 and 2 of FIG. 14, so as to perform a subsequent processing of quadric surface approximation (and the calculation of ShapeIndex value and Curvedness value). When the two-dimensional image division processing is used as each processing shown in FIG. 9, the regions of the three-dimensional model corresponding to the regions of classes 3 to 5 for example, among the regions of classes 1 to 5 in the two-dimensional image shown in FIG. 14, are detected as the regions containing dense data which is useful in detecting of a locally protruding lesion. Thus, the CPU 22 uses a cubic region of a relatively small size as a lesion detection reference for the regions of the three-dimensional model corresponding to the regions at classes 3 and 5 of FIG. 14, so as to perform a subsequent processing of quadric surface approximation (and the calculation of ShapeIndex value and Curvedness value).

In addition, the CPU 22 performs a processing for calculating a ShapeIndex value and a Curvedness value on each voxel in the region to be processed which was set at Step S2 of FIG. 3, based on the lesion detection reference set by the lesion detection reference setting processing shown in FIG. 8 (Step S4 of FIG. 3). Herein, the method of quadric surface approximation and calculation of ShapeIndex value and Curvedness value may be generally the same as that used in the first embodiment, which will not be explained in the present embodiment.

Then, the CPU 22 performs the above processings at Step S5 and Step S6 of FIG. 3 described as the contents of the first embodiment, and then ends a series of the processings. That is, the CPU 22 detects a voxel having a locally protruding lesion based on the ShapeIndex value and the Curvedness value, and also based the detection result, controls the display processing section 28 to indicate the position of each voxel where the existence of a locally protruding lesion is suggested, and then ends a series of the processings.

As a result, the monitor 4 displays a three-dimensional model of an object in which the position of a locally protruding portion such as a polyp is easily recognizable by a user.

The medical image processing apparatus 3 of the present embodiment performs a series of the above described processings shown in FIG. 3, FIG. 8, and FIG. 9, so as to improve the accuracy in the detection of a locally protruding lesion in a three-dimensional model as compared to the prior art.

The two-dimensional image division processing which is a part of the lesion detection reference setting processing shown in FIG. 8 is not limited to the respective processings shown in FIG. 9, and may be the respective ones shown in FIG. 15 for example.

The two-dimensional image division processing shown in FIG. 15 will be explained below.

The CPU 22 first extracts the edges in the two-dimensional image which was used in the estimation of the three-dimensional model by a filtering processing, as the two-dimensional image division processing (Step S131 of FIG. 15), and also calculates the length of each of the extracted edges (Step S132 of FIG. 15). Specifically, the CPU 22 extracts each edge at the position shown in FIG. 16 in the two-dimensional image shown in FIG. 10 for example, and also calculates the length of each of the edges.

Next, the CPU 22 detects the longest edge among the edges in the part of the two-dimensional image which is not divided into regions yet (Step S133 of FIG. 15), and also extracts the maximum horizontal coordinate x_max, the minimum horizontal coordinate x_min, the maximum vertical coordinate y_max, and the minimum vertical coordinate y_min among the coordinates on the two-dimensional image in which the one edge is located (Step S134 of FIG. 15). Specifically, when the entire region of the two-dimensional image is not divided into regions yet, as shown in FIG. 17, the CPU 22 detects the edge E11 which is the longest edge among the edges extracted by the processing shown at Step S131 of FIG. 15. Next, as shown in FIG. 17, the CPU 22 extracts the maximum horizontal coordinate x_max1, the minimum horizontal coordinate x_min1, the maximum vertical coordinate y_max1, and the minimum vertical coordinate y_min1 among the coordinates on the two-dimensional image in which the edge E11 is located. In the present embodiment, the following explanation is based on the assumption that the pixel at the upper left position of a two-dimensional image is set to be the origin coordinate.

Also, the CPU 22 divides the rectangular region surrounded by the four coordinates of the x_max, the x_min, the y_max, and the y_min as a region which belongs to one class (Step S135 of FIG. 15). Specifically, the CPU 22 divides the rectangular region surrounded by the four coordinates of the x_max1, the x_min1, the y_max1, and the y_min1 which were extracted based on the coordinates of the edge E11 as a region which belongs to class 1.

Then, the CPU 22 detects if an edge is included in the part of the two-dimensional image which is not divided into regions yet. When the CPU 22 detects that an edge is included in the part of the two-dimensional image which is not divided into regions yet (Step S136 of FIG. 15), CPU 22 again performs the processings from Step S133 to Step S135 of FIG. 15, so as to divide the two-dimensional image into regions. Specifically, after the CPU 22 divides the region in class 1, as shown in FIG. 18, the CPU 22 detects an edge E12 which is the longest edge in the part of the two-dimensional image which is other than the part divided as the region in class 1 and is not divided into regions yet. Furthermore, the CPU 22 extracts the four coordinates of the maximum horizontal coordinate x_max2, the minimum horizontal coordinate x_min2, the maximum vertical coordinate y_max2, and the minimum vertical coordinate y_min2 based on the coordinates of the edge E12, and also divides the rectangular region surrounded by the extracted four coordinates as a region which belongs to class 2. Then, the CPU 22 repeats the above described processings until the part of the two-dimensional image which is not divided into regions yet includes no more edges.

When the CPU 22 detects that the part of the two-dimensional image which is not divided into regions yet includes no more edges (Step S136 of FIG. 15), after setting the remaining part of the two-dimensional image which is not divided into regions yet to be a region belonging to one class (Step S137 of FIG. 15), the CPU 22 ends the two-dimensional image division processing. Specifically, the CPU 22 performs the above described two-dimensional image division processing, so as to divide the two-dimensional image shown in FIG. 10 into, as shown in FIG. 19, regions of eight classes: the regions of classes 1 to 7 that includes edges in the two-dimensional image; and the region of class 8 that does not include an edge in the two-dimensional image, for example.

When each processing in the two-dimensional image division processing shown in FIG. 15 is used, for example, the regions of three-dimensional model corresponding to the regions of classes 1 to 7 of FIG. 19 that includes edges in the two-dimensional image are detected as the regions containing dense data which is useful in the detection of a locally protruding lesion. Thus, the CPU 22 uses a cubic region of a relatively small size as the lesion detection reference for the regions of the three-dimensional model corresponding to the regions of classes 1 to 7 of FIG. 19 for quadric surface approximation (and the calculation of ShapeIndex value and Curvedness value). Also When each processing in the two-dimensional image division processing shown in FIG. 15 is used, for example, the region of three-dimensional model corresponding to the region of class 8 of FIG. 19 that does not include an edge in the two-dimensional image is detected as a region containing sparse data which is useful in detecting of a locally protruding lesion. Thus, the CPU 22 uses a cubic region of a relatively large size as the lesion detection reference for the region of the three-dimensional model corresponding to the region of classes 8 of FIG. 19 for quadric surface approximation (and the calculation of ShapeIndex value and Curvedness value).

The two-dimensional image division processing which is included in a part of the lesion detection reference setting processing shown in FIG. 8 is not limited to the respective processings shown in FIG. 9 and FIG. 15, and may be the respective ones shown in FIG. 20 for example.

The two-dimensional image division processing shown in FIG. 20 will be explained below.

The CPU 22 first extracts the edges in the two-dimensional image which was used in the estimation of the three-dimensional model by a filtering processing, as the two-dimensional image division processing (Step S141 of FIG. 20). In the processing, the CPU 22 extracts each edge at the position shown in FIG. 16 in the two-dimensional image shown in FIG. 10, for example.

Next, the CPU 22 expands each of the edges extracted in the processing at Step S141 of FIG. 20 (Step S142 of FIG. 20). In other words, the CPU 22 detects the pixels along each edge which was extracted in the processing at Step S141 of FIG. 20 as the pixel that constitutes a part of each edge, so as to increase the line thickness of the one edge. In the processing, the CPU 22 expands each edge at the position shown in FIG. 16 to the condition shown in FIG. 21 for example.

Then, the CPU 22 classifies each expanded edge with reference to the condition of each edge before the expansion (Step S143 of FIG. 20), and also classifies the part which is not classified yet as a region of one class (Step S144 of FIG. 20). Specifically, the CPU 22 classifies the edges that were expanded into the condition shown in FIG. 21 into classes 1 to 9 for example, as shown in FIG. 22, and also classifies the part which is not classified yet into class 10.

When each processing in the two-dimensional image division processing shown in FIG. 20 is used, for example, the regions of the three-dimensional model corresponding to the regions in classes 1 to 9 of FIG. 22 which are the regions including edges in the two-dimensional image are detected as the regions containing dense data which is useful in the detection of a locally protruding lesion. Thus, the CPU 22 uses a cubic region of a relatively small size as the lesion detection reference for the regions of the three-dimensional model corresponding to the regions of classes 1 to 9 of FIG. 22 for quadric surface approximation (and the calculation of ShapeIndex value and Curvedness value). When each processing in the two-dimensional image division processing shown in FIG. 20 is used, for example, the region of the three-dimensional model corresponding to the region in class 10 of FIG. 22 which is the region including no edge in the two-dimensional image is detected as a region containing sparse data which is useful in detecting of a locally protruding lesion. Thus, the CPU 22 uses a cubic region of a relatively large size as the lesion detection reference for the region of the three-dimensional model corresponding to the region of class 10 of FIG. 22 for quadric surface approximation (and the calculation of ShapeIndex value and Curvedness value).

The two-dimensional image division processing which is included in a part of the lesion detection reference setting processing shown in FIG. 8 is not limited to the respective processings shown in FIG. 9, FIG. 15, and FIG. 20, and may be an image division processing in which a grayscale value of each pixel in a two-dimensional image is extracted as the image information according to the grayscale of each pixel in the two-dimensional image which was used in the estimation of a three-dimensional model, and the grayscale values are used for classification, for example.

In the case, the CPU 22 divides regions by classifying the pixels that have close grayscale values to each other into the same class, based on the grayscale value of each pixel included in the two-dimensional image which was used in the estimation of the three-dimensional model, for example. Then the CPU 22 uses a cubic region of a relatively large size as the lesion detection reference for the regions of the three-dimensional model corresponding to the regions that include pixels of smaller grayscale values in the two-dimensional image for quadric surface approximation (and the calculation of ShapeIndex value and Curvedness value). And the CPU 22 uses a cubic region of a relatively small size as the lesion detection reference for the regions of the three-dimensional model corresponding to the regions that include pixels of larger grayscale values in the two-dimensional image for quadric surface approximation (and the calculation of ShapeIndex value and Curvedness value).

Third Embodiment

Figure 23:
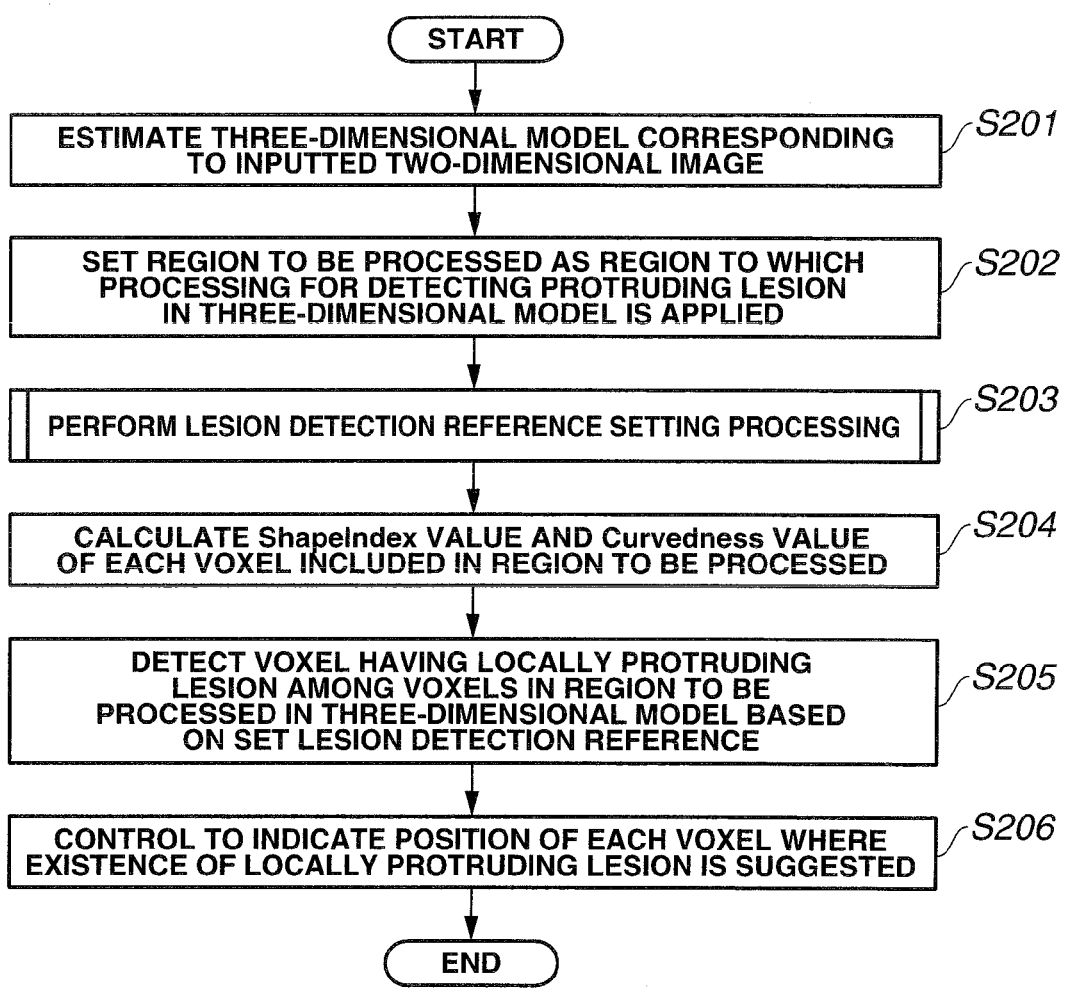
FIG. 23 is a flowchart showing the procedure of the processing performed by the medical image processing apparatus of FIG. 1 in a third embodiment.
Figure 24:
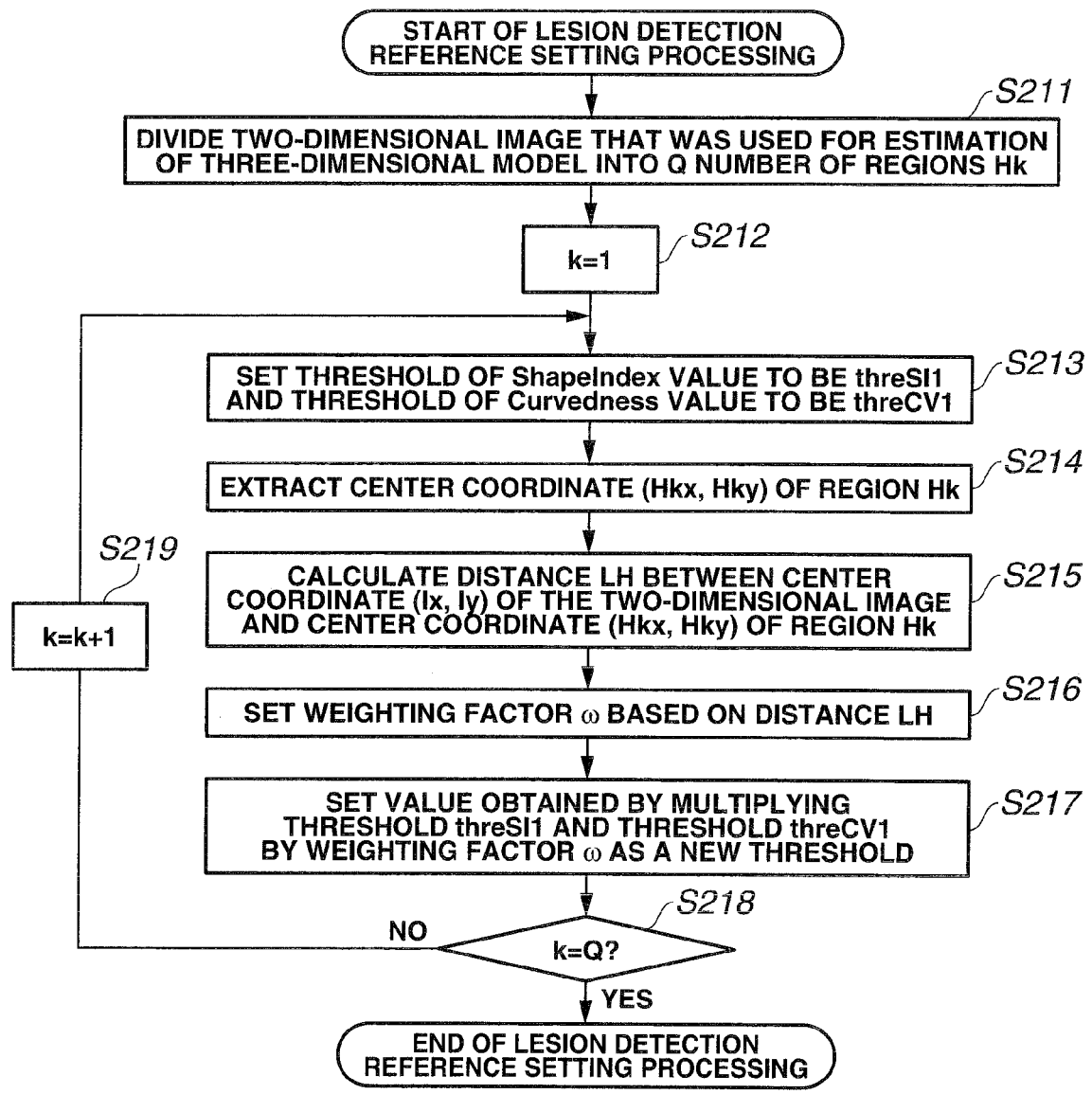
FIG. 24 is a flowchart showing an example of processing performed in the third embodiment as a lesion detection reference setting processing in FIG. 23.
Figure 25:
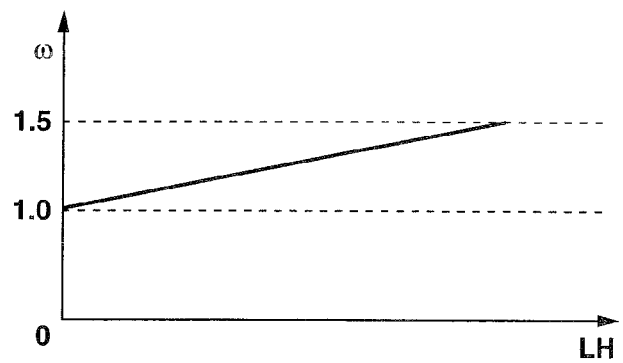
FIG. 25 is a diagram showing the correlation between a distance LH calculated in the processing of FIG. 24 and a weighting factor ω.
Figure 26:
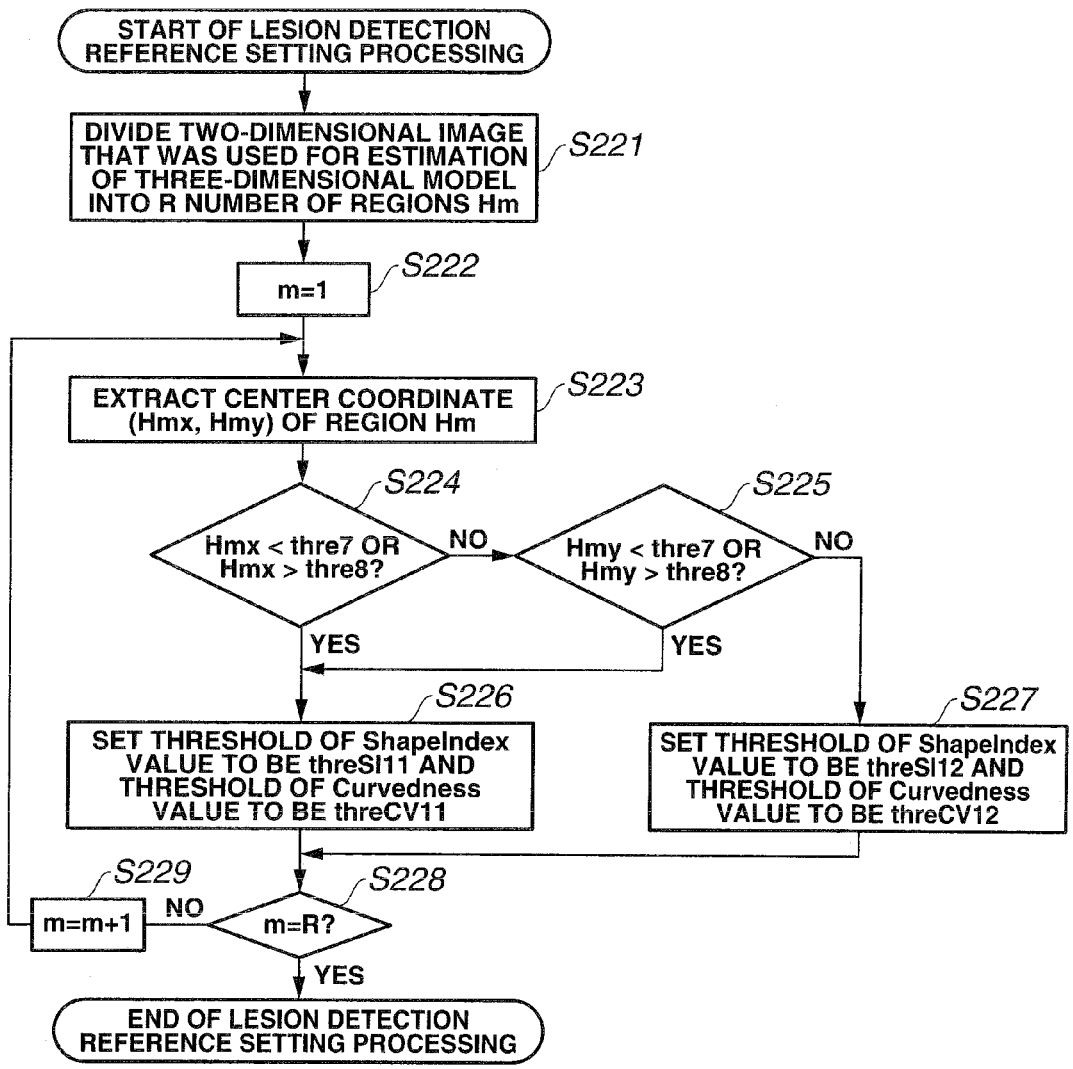
FIG. 26 is a flowchart showing an example, different from that of FIG. 24, of the processing performed as the lesion detection reference setting processing in FIG. 23 in the third embodiment.
Figure 27:
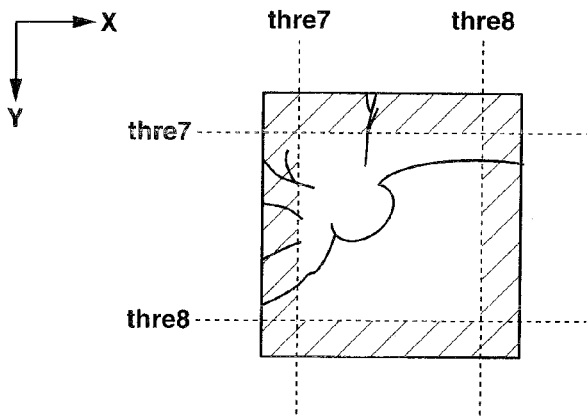
FIG. 27 is a diagram showing the region detected as an edge portion of a two-dimensional image by the processing of FIG. 26.

FIGS. 23 to 27 show a third embodiment of the present invention. FIG. 23 is a flowchart showing the procedure of the processing performed by the medical image processing apparatus of FIG. 1 in a third embodiment. FIG. 24 is a flowchart showing an example of processing performed in the third embodiment as a lesion detection reference setting processing in FIG. 23. FIG. 25 is a diagram showing the correlation between a distance LH calculated in the processing of FIG. 24 and a weighting factor ω. FIG. 26 is a flowchart showing an example, different from that of FIG. 24, of the processing performed as the lesion detection reference setting processing in FIG. 23 in the third embodiment. FIG. 27 is a diagram showing the region detected as an edge portion of a two-dimensional image by the processing of FIG. 26.

The part having the same configuration as those of the first embodiment and the second embodiment will not be explained below. Also, the components similar to those of the first embodiment and the second embodiment are designated with the same numeral references, and will not be explained below. The endoscope system 1 used in the present embodiment has the same configuration as those of the first embodiment and the second embodiment.

Next, the operations for image processing by the medical image processing apparatus 3 will be explained below.

The CPU 22 performs the processings similar to those at Step S1 and Step S2 of FIG. 3 which were already explained in the first embodiment as the processings at Step S201 and Step S202 of FIG. 23, and then performs a lesion detection reference setting processing (Step S203 of FIG. 23) which will be explained below, as a processing for setting the lesion detection reference to be used in the detection of a locally protruding lesion in a three-dimensional model.

The CPU 22 as an image dividing section first divides the two-dimensional image which was used in the estimation of the three-dimensional model into the Q number of regions Hk (1≦k≦Q) (Step S211 of FIG. 24), and sets the variable k=1 (Step S212 of FIG. 24), and also sets the threshold of ShapeIndex value to be threSI1 and the threshold of Curvedness value to be threCV1 (Step S213 of FIG. 24), as the lesion detection reference setting processing.

Next, the CPU 22 as an image position detection section extracts the center coordinate (Hkx, Hky) of the region Hk (Step S214 of FIG. 24), and also calculates a distance LH between the center coordinate (Hkx, Hky) and the center coordinate (Ix, Iy) of the two-dimensional image so as to detect the positional relationship between the region Hk and a predetermined position on the two-dimensional image (Step S215 of FIG. 24). In the present embodiment, the following explanation is based on the assumption that the pixel at the upper left position of a two-dimensional image is set to be the origin coordinate.

Moreover, the CPU 22 sets a weighting factor ω based on the distance LH (Step S216 of FIG. 24), and also sets the value obtained by multiplying the threshold threSI1 and the threshold threCV1 by the weighting factor ω as a new threshold (Step S217 of FIG. 24).

Furthermore, the CPU 22 determines if the above described processings were performed on all of the Q number of regions Hk or not, that is the variable k=Q or not. When the CPU 22 detects that the variable k is not equal to Q (Step S218 of FIG. 24), the CPU 22 adds 1 to the variable k (Step S219 of FIG. 24), and then again performs the above described processings from Step S213 to Step S218 of FIG. 24. When the CPU 22 detects that the variable k is equal to Q (Step S218 of FIG. 24), the CPU 22 holds the value which was obtained for each region Hk by multiplying the threshold threSI1 and the threshold threCV1 by the weighting factor ω as the lesion detection reference for the regions of the three-dimensional model corresponding to each of the regions Hk, and then ends the lesion detection reference setting processing. The weighting factor ω in the present embodiment is a value that linearly increases depending on the value of the distance LH, for example, as shown in FIG. 25.

Then, the CPU 22 calculates a ShapeIndex value and a Curvedness value of each voxel included in a region to be processed (Step S204 of FIG. 23). That is, the CPU 22 performs quadric surface approximation using the predetermined cubic region size, so as to calculate a local partial differential coefficient for each region of the three-dimensional model based on the result of the quadric surface approximation, and also calculate a ShapeIndex value that represents the unevenness of each voxel of the three-dimensional model and a Curvedness value that represents the curvature of each voxel of the three-dimensional model, based on the local partial differential coefficient.

The above described ShapeIndex value is a value that represents the unevenness of each voxel of the three-dimensional model, and is shown as a value which is 0 or more and 1 or less. Specifically, one voxel (or one group of voxels) in a three-dimensional model that has a ShapeIndex value close to 0 suggests an existence of a concave shape; while a ShapeIndex value close to 1 suggests an existence of a convex shape. The above described Curvedness value is a value that represents the curvature of each voxel of the three-dimensional model. Specifically, one voxel (or one group of voxels) in a three-dimensional model that has a smaller Curvedness value suggests an existence of a sharply bended curved surface; while a larger Curvedness valve suggests an existence of a loosely bended curved surface.

The CPU 22 detects a voxel having a locally protruding lesion among the voxels in the region to be processed in the three-dimensional model, based on the lesion detection reference set at Step S203 of FIG. 23 and the ShapeIndex value and the Curvedness value calculated at Step S204 of FIG. 23 (Step S205 of FIG. 23).

Then, the CPU 22 performs the processing similar to that at Step S6 of FIG. 3 which was already explained in the first embodiment as the processings shown at Step S206 of FIG. 23, and then ends the series of the processings. That is, the CPU 22 controls the display processing section 28 to indicate the position of each voxel where the existence of a locally protruding lesion is suggested based on the detection result by the processing at Step S205 of FIG. 23, and then ends a series of the processings.

As a result, the monitor 4 displays the image of the three-dimensional model of an object in which the position of a locally protruding portion such as a polyp is easily recognizable by a user.

Meanwhile, when a three-dimensional model is estimated using a two-dimensional image, sometimes the region of the three-dimensional model that corresponds to an edge portion of the two-dimensional image is estimated as a rounded region. Then the CPU 22 uses the lesion detection reference setting processing shown in FIG. 24, so as to detect a voxel having a locally protruding lesion based on a detection reference which is more strict as compared to the lesion detection reference for the regions of the three-dimensional model corresponding to the part other than the edge portion of the two-dimensional image as the lesion detection reference for the regions of the three-dimensional model corresponding to the edge portion of the two-dimensional image, that is, by excluding the above described region which is estimated as a rounded region from the region to be processed. As a result, the medical image processing apparatus 3 of the present embodiment improves the accuracy in the detection of a locally protruding lesion which is included in the three-dimensional model estimated using a two-dimensional image, particularly in the region of the three-dimensional model corresponding to the edge portion of the two-dimensional image, compared to the prior art.

The lesion detection reference setting processing shown in FIG. 23 is not limited to the respective processings shown in FIG. 24, and may be the respective ones shown in FIG. 26 for example, as a processing that provides generally the same effect as that obtained in the above described present embodiment.

The lesion detection reference setting processing shown in FIG. 26 will be explained below.

The CPU 22 as an image dividing section first divides the two-dimensional image which was used in the estimation of the three-dimensional model into the R number of regions Hm (1≦m≦R) (Step S221 of FIG. 26), and sets the variable m=1 (Step S222 of FIG. 26), and also extracts the center coordinate (Hmx, Hmy) of the region Hm (Step S223 of FIG. 26), as a lesion detection reference setting processing.

Next, the CPU 22 as an image position detection section determines if the coordinate (Hmx, Hmy) is included in the edge portion of the two-dimensional image in order to detect the positional relationship between the region Hm and a predetermined position on the two-dimensional image, based on the extracted center coordinate of the region Hm. Specifically, the CPU 22 detects if Hmx<thre7 or Hmx>thre8 is true or not. When the CPU 22 detects that one of Hmx<thre7 or Hmx>thre8 is true (Step S224 of FIG. 26), the CPU 22 performs the processing at Step S226 of FIG. 26 which will explained later. When the CPU 22 detects that none of Hmx<thre7 or Hmx>thre8 is true (Step S224 of FIG. 26), the CPU 22 further detects if Hmy<thre7 or Hmy>thre8 is true or not.

When the CPU 22 detects that one of Hmy<thre7 or Hmy>thre8 is true (Step S225 of FIG. 26), the CPU 22 performs the processing at Step S226 of FIG. 26 which will explained later. When the CPU 22 detects that none of Hmy<thre7 and Hmy>thre8 is true (Step S225 of FIG. 26), the CPU 22 performs the processing at Step S227 of FIG. 26 which will explained later.

The CPU 22 as a lesion detection reference setting section sets the threshold of a ShapeIndex value to be threSI11 and the threshold of a Curvedness value to be threCV11 (Step S226 of FIG. 24) when the center coordinate of the region Hm (Hmx, Hmy) satisfies one of the above described conditions shown at Step S224 and Step S225 of FIG. 26. Also, the CPU 22 as a lesion detection reference detecting section sets the threshold of a ShapeIndex value to be threSI12<(threSI11) and the threshold of a Curvedness value to be threCV12<(threCV11) (Step S227 of FIG. 24) when the center coordinate of the region Hm (Hmx, Hmy) satisfies none of the above described conditions shown at Step S224 and Step S225 of FIG. 26.

In other words, the CPU 22 sets the threshold of a ShapeIndex value to be threSI11 and the threshold of a Curvedness value to be threCV11 when the center coordinate of the region Hm (Hmx, Hmy) is included in the coordinates in the shaded region shown in FIG. 27 for example, which is the edge portion of the two-dimensional image. Also, the CPU 22 sets the threshold of a ShapeIndex value to be threSI12 and the threshold of a Curvedness value to be threCV12 when the center coordinate of the region Hm (Hmx, Hmy) is included in the coordinates in the region other than the shaded region shown in FIG. 27 for example, which is the region other than the edge portion of the two-dimensional image.

Furthermore, the CPU 22 determines if the above described processings were performed on all of the R number of regions Hm or not, that is the variable m=R or not. When the CPU 22 detects that the variable m is not equal to R (Step S228 of FIG. 26), the CPU 22 adds 1 to the variable m (Step S229 of FIG. 26), and then again performs the above described processings from Step S223 to Step S228 of FIG. 26. When the CPU 22 detects that the variable m is equal to R (Step S228 of FIG. 26), the CPU 22 holds the threshold of ShapeIndex value and the threshold of Curvedness value which were set for each region Hm as the lesion detection reference for the regions of the three-dimensional model corresponding to each of the regions Hm, and then ends the lesion detection reference setting processing.

The lesion detection reference setting processing shown in FIG. 23 is not limited to the respective processings shown in FIG. 24 and FIG. 26, and may be a processing based on a grayscale value of a two-dimensional image which is used in the estimation of a three-dimensional model for example, as a processing which improves the accuracy in the detection of a locally protruding lesion in a three-dimensional model as compared to the prior art. Specifically, the CPU 22 divides the two-dimensional image used in the estimation of a three-dimensional model into a plurality of regions, and calculates the mean grayscale value of each of the plurality of regions. Then based on the calculation result of the mean grayscale value for each of the plurality of regions, the CPU 22 sets the threshold of ShapeIndex value and the threshold of Curvedness value to be relatively large values for a region of a three-dimensional model which corresponds to the region having a small grayscale value in the two-dimensional image, that is, for a region of the three-dimensional model that contains sparse data that is useful in the detection of a protruding lesion, for example. While, based on the calculation result of the mean grayscale value for each of the plurality of regions, the CPU 22 sets the threshold of ShapeIndex value and the threshold of Curvedness value to be relatively small values for a region of a three-dimensional model which corresponds to the region having a large grayscale value in the two-dimensional image, that is, for a region of the three-dimensional model that contains dense data that is useful in the detection of a protruding lesion, for example.

The present invention is not limited to the above described embodiments, and needless to say, various changes and applications can be made without departing from the spirit of the invention.

What is claimed is:

1. A medical image processing apparatus, comprising:
   a three-dimensional model estimating section for estimating a three-dimensional model of an object based on a two-dimensional image of the object which is obtained by picking up an inside of the object;
   an image dividing section for dividing the two-dimensional image into a plurality of regions each of which includes at least one or more pixels;
   a feature value calculation section for calculating a feature value according to a grayscale of each pixel in one of the plurality of regions and a frequency component of the one region; and
   a lesion detection reference setting section for performing a threshold determination for determining whether data included in a three-dimensional model which corresponds to the one region is sparse or dense with respect to each of the feature value according to the grayscale and the frequency component, and further setting a lesion detection reference which is used when detecting a locally protruding lesion in the three-dimensional model which corresponds to the one region based on a result of the threshold determination.

2. The medical image processing apparatus according to claim 1, wherein the feature value according to the grayscale is a mean value of grayscale values of each pixel included in the one region.

3. The medical image processing apparatus according to claim 1, wherein the feature value according to the grayscale is a variance of grayscale values of each pixel included in the one region.

4. The medical image processing apparatus according to claim 2, wherein the feature value according to the grayscale is a variance of grayscale values of each pixel included in the one region.

5. The medical image processing apparatus according to claim 1, wherein
the lesion detection reference is the size of a cubic region which is used in quadric surface approximation in the three-dimensional model which corresponds to the one region, and
the lesion detection reference setting section increases and decreases the size of the cubic region according to a result of the threshold determination.

6. The medical image processing apparatus according to claim 2, wherein
the lesion detection reference is the size of a cubic region which is used in quadric surface approximation in the three-dimensional model which corresponds to the one region, and
the lesion detection reference setting section increases and decreases the size of the cubic region according to a result of the threshold determination.

7. The medical image processing apparatus according to claim 3, wherein
the lesion detection reference is the size of a cubic region which is used in quadric surface approximation in the three-dimensional model which corresponds to the one region, and
the lesion detection reference setting section increases and decreases the size of the cubic region according to a result of the threshold determination.

8. The medical image processing apparatus according to claim 4, wherein
the lesion detection reference is the size of a cubic region which is used in quadric surface approximation in the three-dimensional model which corresponds to the one region, and
the lesion detection reference setting section increases and decreases the size of the cubic region according to a result of the threshold determination.

9. The medical image processing apparatus according to claim 1, wherein the locally protruding lesion is a polyp.

10. A medical image processing method, comprising:
a three-dimensional model estimating step for estimating a three-dimensional model of an object based on a two-dimensional image of the object obtained by picking up an inside of the object;
an image dividing step for dividing the two-dimensional image into a plurality of regions each of which includes at least one or more pixels;
a feature value calculating step for calculating a feature value according to a grayscale of each pixel included in one of the plurality of regions and a frequency component of the one region; and
a lesion detection reference setting step for performing a threshold determination for determining whether data included in a three-dimensional model that corresponds to the one region is sparse or dense with respect to each of the feature value according to the grayscale and the frequency component, and further setting a lesion detection reference which is used when detecting a locally protruding lesion in the three-dimensional model which corresponds to the one region based on a result of the threshold determination.

11. The medical image processing method according to claim 10, wherein the feature value according to the grayscale is a mean value of grayscale values of each pixel included in the one region.

12. The medical image processing method according to claim 10, wherein the feature value according to the grayscale is a variance of grayscale values of each pixel included in the one region.

13. The medical image processing method according to claim 11, wherein the feature value according to the grayscale is a variance of grayscale values of each pixel included in the one region.

14. The medical image processing method according to claim 10, wherein the lesion detection reference is the size of a cubic region which is used in quadric surface approximation in the three-dimensional model which corresponds to the one region, and
the lesion detection reference setting step increases and decreases the size of the cubic region according to a result of the threshold determination.

15. The medical image processing method according to claim 11, wherein the lesion detection reference is the size of a cubic region which is used in quadric surface approximation in the three-dimensional model which corresponds to the one region, and
the lesion detection reference setting step increases and decreases the size of the cubic region according to a result of the threshold determination.

16. The medical image processing method according to claim 12, wherein the lesion detection reference is the size of a cubic region which is used in quadric surface approximation in the three-dimensional model which corresponds to the one region, and
the lesion detection reference setting step increases and decreases the size of the cubic region according to a result of the threshold determination.

17. The medical image processing method according to claim 13, wherein the lesion detection reference is the size of a cubic region which is used in quadric surface approximation in the three-dimensional model which corresponds to the one region, and
the lesion detection reference setting step increases and decreases the size of the cubic region according to a result of the threshold determination.

18. The medical image processing method according to claim 10, wherein the locally protruding lesion is a polyp.

* * * * *